United States Patent
Xu et al.

(10) Patent No.: US 9,625,460 B2
(45) Date of Patent: Apr. 18, 2017

(54) METHODS AND COMPOSITIONS FOR USE OF NEUTROPHIL ELASTASE AND PROTEINASE 3 AS DIAGNOSTIC BIOMARKERS

(71) Applicant: THE UNIVERSITY OF HONG KONG, Hong Kong (CN)

(72) Inventors: Aimin Xu, Hong Kong (CN); Yudong Wang, Hong Kong (CN); Ling Zhong, Hong Kong (CN); Siu Ling Lam, Hong Kong (CN)

(73) Assignee: VERSITECH LIMITED, Hong Kong (CN)

(*) Notice: Subject to any disclaimer, the term of this patent is extended or adjusted under 35 U.S.C. 154(b) by 0 days.

(21) Appl. No.: 14/725,101

(22) Filed: May 29, 2015

(65) Prior Publication Data

US 2015/0346203 A1 Dec. 3, 2015

Related U.S. Application Data

(60) Provisional application No. 62/004,969, filed on May 30, 2014.

(51) Int. Cl.
*G01N 33/573* (2006.01)
*G01N 33/52* (2006.01)
*G01N 33/564* (2006.01)

(52) U.S. Cl.
CPC .......... *G01N 33/573* (2013.01); *G01N 33/52* (2013.01); *G01N 33/564* (2013.01); *G01N 2333/966* (2013.01); *G01N 2333/96433* (2013.01); *G01N 2800/042* (2013.01)

(58) Field of Classification Search
None
See application file for complete search history.

(56) References Cited

U.S. PATENT DOCUMENTS

| 6,569,876 B1 * | 5/2003 | Cheronis .............. C07D 233/72 514/20.4 |
| 2016/0011207 A1 * | 1/2016 | Oh ..................... G01N 33/6893 514/20.4 |

OTHER PUBLICATIONS

Korkmaz et al. J. Biological Chemistry 2002 vol. 277, p. 39074-39081.*
Witko-Sarsat et al. performed the same (J. Am. Socl. Nephrol. 1999 vol. 10, p. 1224-1233).*
Bae et al. Endocrine Research 2012 vol. 37, 35-45.*
Jackson et al. Diabetes Research 1989 vol. 10, p. 135-138).*

* cited by examiner

*Primary Examiner* — Jacob Cheu
(74) *Attorney, Agent, or Firm* — Saliwanchik, Lloyd & Eisenschenk

(57) ABSTRACT

Methods and compositions for identifying autoimmune diabetes are provided. One aspect provides a method for the evaluation of risk and progression of autoimmune diabetes in mammalian subjects. The method includes measuring the enzymatic activities and/or protein concentrations of neutrophil elastase and proteinase 3 in a subject and comparing the measured levels of these proteases to respective reference levels.

20 Claims, 11 Drawing Sheets

A

B

METHODS AND COMPOSITIONS FOR USE OF NEUTROPHIL ELASTASE AND PROTEINASE 3 AS DIAGNOSTIC BIOMARKERS

CROSS-REFERENCE TO RELATED APPLICATION

This application claims the benefit of U.S. Provisional Application Ser. No. 62/004,969, filed May 30, 2014, which is hereby incorporated by reference in its entirety.

FIELD OF THE INVENTION

Aspects of the present invention are generally directed to the use of neutrophil elastase and proteinase 3 thereof as diagnostic biomarkers, for example, in autoimmune diabetes.

BACKGROUND OF THE INVENTION

The prevalence of diabetes, which is characterized by hyperglycemia resulting from defects in insulin secretion and/or actions, is reaching epidemic levels globally (American Diabetes Association, *Diabetes care* 36 Suppl 1:S67-74 (2013)). The International Diabetes Federation (IDF) estimated that there are currently 382 million diabetic patients worldwide, with ~46% remaining undiagnosed until they develop diabetic complications. Over 548 billion USD was spent on diabetes healthcare in 2013 (International Diabetes Federation, IDF Diabetes Atlas, $6^{th}$ edition/2013 update (2013)). According to the latest epidemiological survey conducted in Mainland China, there are currently 113.9 million adults with diabetes and 493.4 million adults with prediabetes (Xu et al., *JAMA* 310:948-959 (2013)). The vast majority of cases of diabetes fall into two broad etiopathogenetic categories: type 1 diabetes (T1D), an autoimmune disease characterized with insulin deficiency due to the immune-mediated destruction of insulin-producing pancreatic β cells, and type 2 diabetes (T2D), a disease characterized by insulin resistance and often associated with obesity or older age (van Belle et al., *Physiological reviews* 91:79-118 (2011)). Although T1D accounts for only about 5-10% of the total cases of diabetes, it is one of the most common chronic diseases in children and adolescents and the most severe type of diabetes, leading to lifelong dependency on daily insulin injections and increased morbidity and mortality due to debilitated microvascular and macrovascular complications (Maahs et al., *Endocrinology and metabolism clinics of North America* 39:481-497 (2010)). Moreover, the incidence of T1D continues to increase worldwide at a rate of nearly 3% per year (Gan et al., *Current problems in pediatric and adolescent health care* 42:269-291 (2012)). Even in those diagnosed with T2D, it is demonstrated that approximately 10% of patients are positive for at least one of the islet autoantibodies, and this group is often referred to as "latent autoimmune diabetes in adults (LADA)" (Naik et al., *The Journal of clinical endocrinology and metabolism* 94:4635-4644 (2009)). These patients share many genetic and immunological similarities with T1D but also have the characteristics of T2D—adult age at onset and initial response to oral hypoglycemic agents; however, LADA patients tend to become insulin dependent and unresponsive to oral medications (Guglielmi et al., *Diabetes/metabolism research and reviews* 28 Suppl 2:40-46 (2012)).

Currently, the detection of autoantibodies against pancreatic β-cell autoantigens, such as insulin autoantibody (IAA), glutamic acid decarboxylase antibody (GADA), insulinoma-associated protein 2 autoantibody (IA-2A), and zinc transporter 8 antibody (ZnT8A), remains the only biomarkers for distinguishing autoimmune diabetes from T2D and detecting those high risk individuals (Lebastchi and Herold, *Cold Spring Harb Perspect Med* 2:a007708 (2012)). However, these autoantibodies are measured by either conventional immunofluorescence staining or with specific radioimmunoassays (Knip et al., *Diabetes* 54 Suppl 2:S125-136 (2005)), both of which are tedious and time-consuming. The radioimmunoassays have concerns of the health risks and disposal issues posed by the use of radioisotopes. Moreover, these autoantibodies from the children are rarely detectable before six months after birth (Ziegler et al., *Diabetes* 48:460-468 (1999)). The diagnostic sensitivity of single autoantibody measurement in T1D patients is as low as 59%-67% (Lebastchi and Herold, 2012). The other immunological assays, including the cellular immunoblot, T-cell proliferation assay, and ELISPOT assay can evaluate cellular immune responses in patients with autoimmune diabetes; however, the limitations of these assays are the requirements for relatively large numbers of peripheral blood mononuclear cell (PBMC) cultures and the need for fresh cells (Lebastchi and Herold, 2012).

BRIEF SUMMARY

It is important to discover new biomarkers for early detection of individuals with high risk of developing T1D as well as for differential diagnosis of autoimmune diabetes (T1D and LADA) from T2D, thereby enabling the adaptation of optimal preventive and therapeutic strategies for the disease. Therefore, it is an object of the present invention to identify subjects that could benefit from early diagnosis and treatment to reduce the risk of developing autoimmune diabetes. It is another object of the invention to provide compositions and methods for assessing the propensity to develop autoimmune diabetes. It is another object to provide compositions and methods for assisting in predicting autoimmune diabetes. It is another object to provide compositions and methods for assisting in the diagnosis of autoimmune diabetes. It is yet another object of the invention to provide methods to reduce the risk of developing autoimmune diabetes.

Compositions and methods for identifying and treating autoimmune diabetes are provided. One aspect of the present invention provides a method for the evaluation of risk and progression of autoimmune diabetes in mammalian subjects. The method comprises measuring the enzymatic activities and/or protein concentrations of at least one of serum neutrophil elastase (NE) and proteinase 3 (PR3) in a subject and comparing the measured levels of these proteases to respective reference levels. The enzymatic activities and protein concentrations of serum NE and PR3 that are higher than the respective reference levels are indicative of an increased risk or propensity of developing autoimmune diabetes.

Still another aspect provides a method for diagnosing or aiding in the diagnosis of autoimmune diabetes in a subject. The method comprises obtaining a blood sample from the subject and measuring the enzymatic activities and protein concentrations of at least one of NE and PR3 contained in the blood sample. The measured enzymatic activities and protein concentrations are compared to respective reference levels. In a preferred aspect, autoimmune diabetes is present if the enzymatic activities and protein concentrations of at least one of NE and PR3 are higher than the respective reference levels. In another preferred embodiment, the enzymatic activities and protein concentrations of at least one of NE and PR3 in the blood samples are analyzed by chromogen-based assays and enzyme-linked immunosorbent assays, respectively.

Additional aspects of the present invention provide methods and compositions for determining that a subject is at risk of developing autoimmune diabetes. In one embodiment, the present invention provides a method for determining whether a subject is at risk of developing autoimmune diabetes, comprising:

obtaining a sample from the subject;

measuring the enzymatic activities and/or protein levels of at least one of neutrophil elastase and proteinase 3 in the sample;

comparing the enzymatic activities and/or protein levels of at least one of neutrophil elastase and proteinase 3 to respective reference levels of enzymatic activities and/or protein levels, wherein the respective reference levels of neutrophil elastase and/or proteinase 3 are obtained from one or more reference subject that does not have autoimmune diabetes; and determining that the subject is at risk of developing autoimmune diabetes when the enzymatic activities and/or protein levels of at least one of neutrophil elastase and/or proteinase 3 contained in the sample are greater than about 20% above the respective reference levels.

Additional aspects of the present invention provide methods and compositions for determining that a subject showing signs of adult onset diabetes is at risk of developing autoimmune diabetes. The methods comprising:

obtaining a sample from the subject;

measuring the enzymatic activities and/or protein levels of at least one of neutrophil elastase and proteinase 3 in the sample;

comparing the enzymatic activities and/or protein levels of at least one of neutrophil elastase and proteinase 3 to respective reference levels of enzymatic activities and/or protein levels, wherein the respective reference levels are obtained from one or more reference subject that does not have autoimmune diabetes; and determining that the subject is at risk of developing an autoimmune diabetes when the enzymatic activities and/or protein levels of at least one of neutrophil elastase and proteinase 3 contained in the sample are greater than about 20% above the respective reference levels.

In some embodiments, the autoimmune diabetes is type 1 diabetes. In some embodiments, the autoimmune diabetes is latent autoimmune diabetes in adults. In some embodiments, the enzymatic activities of neutrophil elastase and proteinase 3 in the sample can be measured by chromogen-based assays. In some embodiments, the protein levels of neutrophil elastase and proteinase 3 in the sample can be measured by immunoassays. In some embodiments, the sample is selected from blood, serum, plasma, urine, saliva, cerebrospinal fluid, tears, tissues, and combinations thereof. In some embodiments, the methods can further include communicating the subject's risk of developing autoimmune diabetes.

In some embodiments, the autoimmune diabetes is type 1 diabetes. In some embodiments, the autoimmune diabetes is latent autoimmune diabetes in adults. In some embodiments, one or more islet-specific autoantibodies, such as GADA, IA2A and/or ZnT8A, are not detectable in the subject. In other embodiments, one or more islet-specific autoantibodies, such as GADA, IA2A and/or ZnT8A, are detectable in the subject. In some embodiments, the subject has one or more risk factors for autoimmune diabetes. In some embodiments, the subject is an infant, a child, an adolescent, or an adult. In some embodiments, the subject is diagnosed with diabetes.

In some embodiments, the methods further comprise treating the subject to reduce the risk of developing autoimmune diabetes when the enzymatic activities and/or protein levels of at least one of neutrophil elastase and proteinase 3 contained in the sample are greater than about 20% above the respective reference levels.

In some embodiments, the subject can be treated with a treatment selected from insulin desensitization, GAD desensitization, heat shock protein 60 (HSP60) desensitization, antagonize Ly6G (GR1 neutrophil marker), neutrophil depletion, antagonize B-cell activating factor (BAFF), promote expression of diabetes-resistant MHC class II molecules, CD3 activation, anti-thymocyte globulin (ATG) therapy, Treg therapy, avoidance of environmental risk factors, immune system modulation, promote β-cell regeneration, B-cell inhibition, CTLA-4 inhibition, tumor necrosis factor-α, IL-1 receptor antagonist, pegylated granulocyte colony-stimulating factor, human recombinant interferon-α, autologous stem cell transplantation, the use of chemical inhibitors or peptide inhibitors of NE/PR3, and a combination thereof.

In some embodiments, the enzymatic activities and/or protein levels of at least one of neutrophil elastase and proteinase 3 contained in the sample are greater than 40% above the respective reference levels. In some embodiments, the treatment can be insulin desensitization, GAD desensitization (Ludvigsson et al. New Engl J Med 359:1909-1920 (2008), heat shock protein 60 (HSP60) desensitization, antagonize Ly6G (GR1 neutrophil marker), neutrophil depletion, antagonize B-cell activating factor (BAFF) (Marino et al. *Diabetes* 61(11):2893-2905 (2012)), promote expression of diabetes-resistant MHC class II molecules (Tian et al., J. Clin. Invest. 114(7):969-978 (2004)), CD3 activation (Herold et al. Diabetes. 62(11):3766-3774 (2013); Herold et al., New Engl J Med 346(22):1692-1698 (2002) (OKT3 antibody)), anti-thymocyte globulin (ATG) therapy (Gitelman et al., The Lancet Diabetes & Endocrinology 1(4):306-316 (2013); Eisenbarth et al. Diabetes Res 2:271-276 (1985)), Treg therapy (Du et al., PLoS One 8(2):e56209 (2013)), avoidance of environmental risk factors, immune system modulation, promote β-cell regeneration, B-cell inhibition, CTLA-4 inhibition, tumor necrosis factor-α (Mastrandrea et al. Diabetes Care 32:1244-1249 (2009)), IL-1 receptor antagonist, pegylated granulocyte colony-stimulating factor, human recombinant interferon-α (Rother et al. Diabetes Care 32:1250-1255 (2009)), autologous stem cell transplantation (Haller et al. Diabetes 58(Supp. 1):A7 (2009) (Abstract); Voltarelli et al. Ann NY Acad Sci 1150: 220-229 (2008); Voltarelli et al. JAMA 297:1568-1576 (2007); Couri et al., JAMA 301:1573-1579 (2009)), the use of chemical inhibitors or peptide inhibitors of NE/PR3, or a combination thereof.

In some embodiments, the autoimmune diabetes is selected from type 1 diabetes and latent autoimmune diabetes in adults. In some embodiments, the enzymatic activities of neutrophil elastase and proteinase 3 in the sample are measured by chromogen-based assays. In some embodiments, the protein levels of neutrophil elastase and proteinase 3 in the sample are measured by immunoassays. In some embodiments, the sample is selected from blood, serum, plasma, urine, saliva, cerebrospinal fluid, tears, tissues or combinations thereof. In some embodiments, the autoimmune diabetes is type 1 diabetes. In some embodiments, the autoimmune diabetes is latent autoimmune diabetes in adults. In some embodiments, the subject is a human subject less than one year old.

In some embodiments, the methods can further comprise communicating the subject's risk of developing autoimmune diabetes.

In some embodiments, the reference levels utilized in the methods of the present invention comprise enzymatic activities and/or protein levels of at least one of neutrophil elastase and proteinase 3 obtained from one or more reference subjects that do not have autoimmune diabetes.

Additional advantages of the disclosed methods and compositions will be set forth in part in the description which follows, and in part will be understood from the description, or may be learned by practice of the disclosed methods and compositions. The advantages of the disclosed methods and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed methods and compositions and, together with the description, serve to explain the principles of the disclosed methods and compositions.

DETAILED DESCRIPTION OF THE INVENTION

Figure 1:
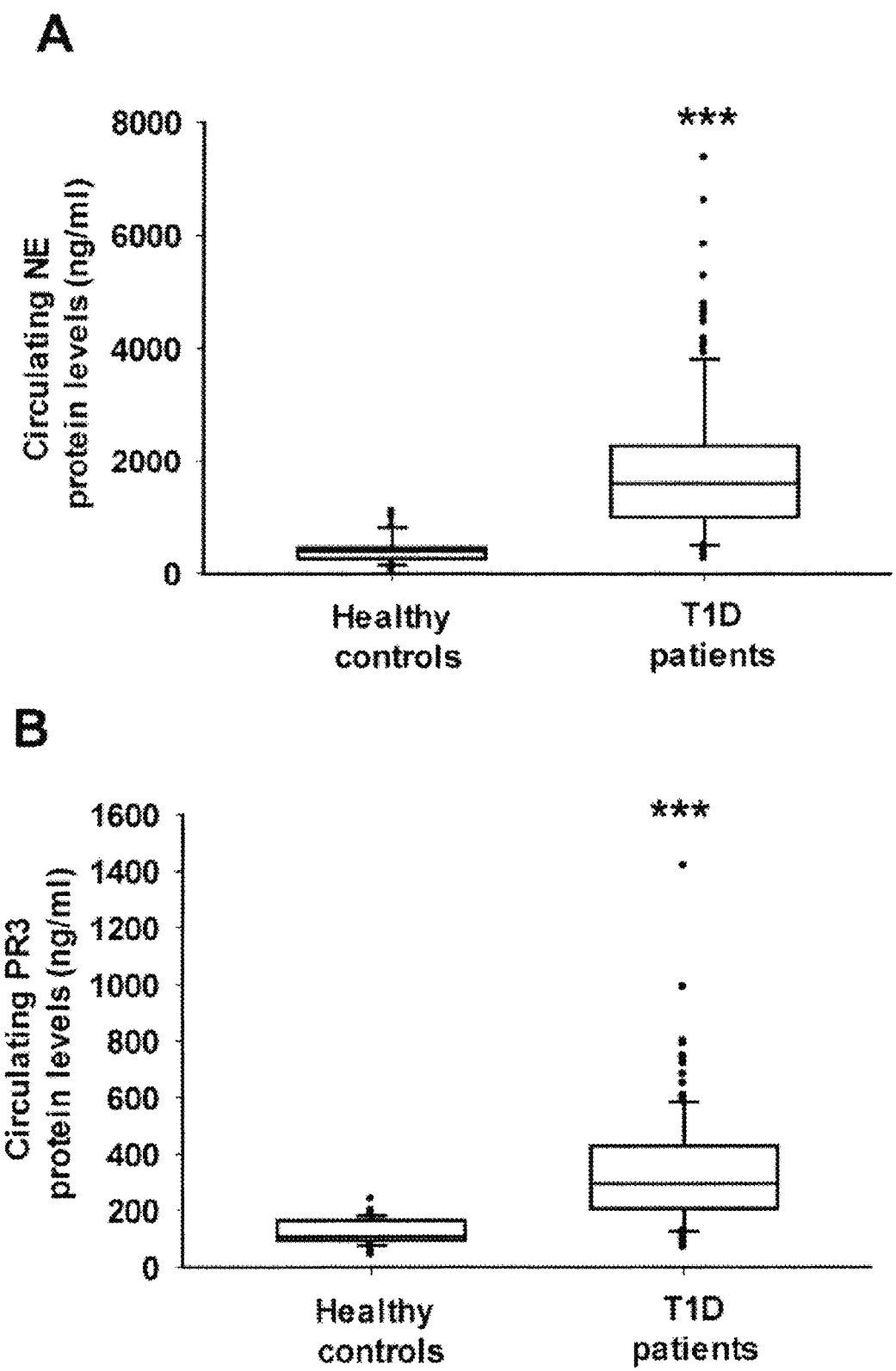
FIG. 1 shows graphs illustrating circulating protein levels of NE (A) and PR3 (B), NE/PR3 enzymatic activities (C), and A1AT protein levels (D) in healthy controls (n=77) and type 1 diabetes (T1D) patients (n=149). The horizontal line in the middle of each box indicates the median value; the top and bottom borders of the boxes represent the $75^{th}$ and $25^{th}$ percentiles, respectively; the whiskers represent the $10^{th}$ and $90^{th}$ percentiles, and the dots represent the outliers. p<0.01, *p<0.001 vs healthy controls.
Figure 1:
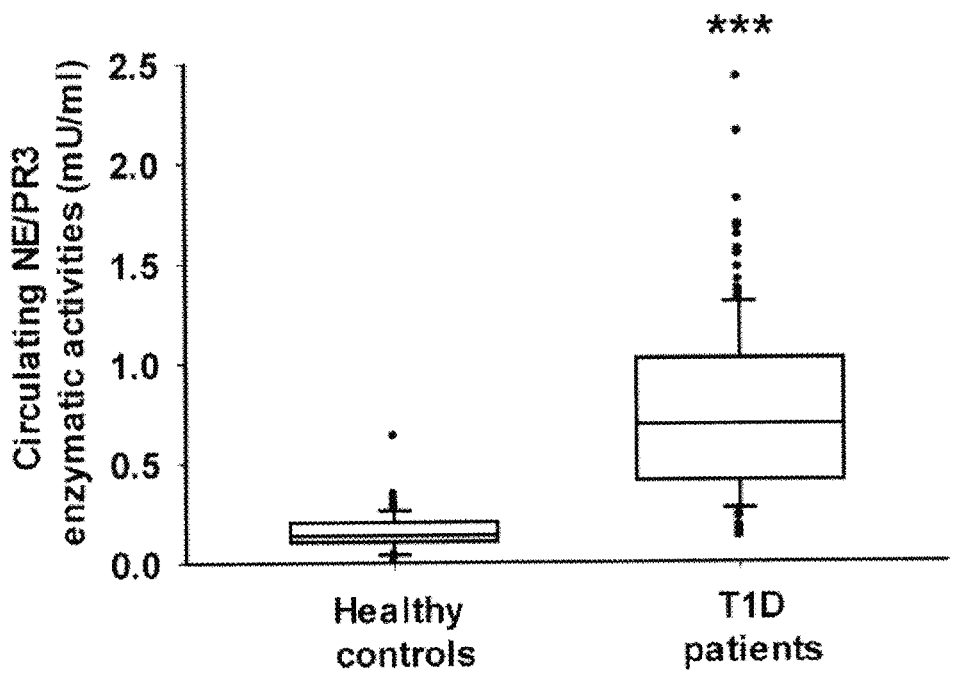
Figure 1:
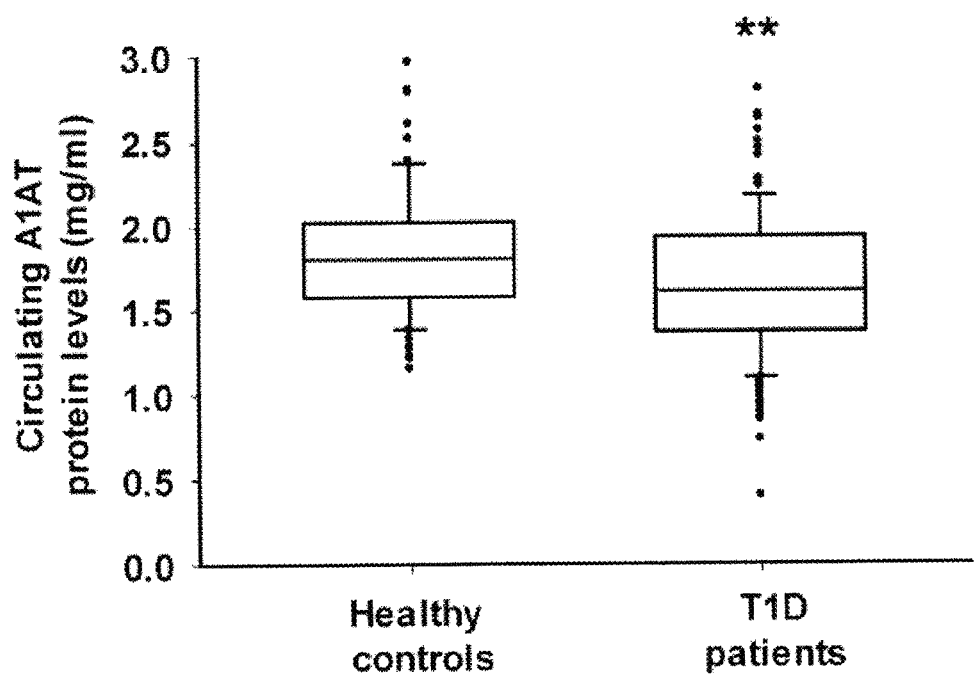

Prevention and delay of the onset of type 1 diabetes (T1D) has long been sought. Strategies and techniques for doing so have been, and continue to be, devised and investigated, but none have been as successful as needed. It is likely that many of these strategies are applied too late, after the disease has already progressed too far to be slowed or stopped. A main problem has been that identification of those at risk has been based on markers and symptoms that are apparent only after much damage has been done, making it more difficult to succeed in slowing or stopping the disease. The present invention solves these problems by allowing identification of at-risk individuals earlier in the development of type 1 diabetes. This identification makes the strategies and techniques for preventing or delaying the onset of type 1 diabetes possible and more effective.

The disclosed methods and compositions may be understood more readily by reference to the following detailed description of particular embodiments and the Example included therein and to the Figures and their previous and following description.

DEFINITIONS

As used herein, the term "autoimmune diabetes" refers to a disease that is related to autoimmunity or is caused by autoimmunity. Representative autoimmune diabetes diseases include, but are not limited to, type 1 diabetes and latent autoimmune diabetes in adults.

As used herein, the term "diagnosis" refers to identifying the type of disease or condition from a set of risk values and/or patient symptoms. This is in contrast to disease prediction, which is to predict the occurrence of a disease or condition before it occurs, disease risk determination, which is to determine a risk of the occurrence of disease or condition before it occurs, and the term "prognosis," which is to predict disease progression at a future point in time, from one or more indicator value(s) at a previous point in time.

As used herein, the term "sample" refers to a biological sample obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred samples include, but are not limited to, blood, serum, plasma, urine, saliva, cerebrospinal fluid, tears or tissues. In addition, one of skill in the art would realize that some samples would be more readily analyzed following a fractionation or purification procedure, for example, separation of whole blood into serum or plasma components.

As used herein, the term "biomarker" refers to substances, such as proteases or peptidase or proteinases or proteins or polypeptides or other biological substances, used as targets for screening samples obtained from a subject.

As used herein, the term "substrate" refers to substances that can be acted on by an enzyme. For example, substrates include compounds conjugated to a chromogenic or fluorogenic group that is released after cleavage. Examples of useful substrates include peptides which are conjugated to a dye group, including, but are not limited to, p-nitroaniline, and can be cleaved at a specific site by proteases.

As used herein, the term "antibody" refers to both polyclonal and monoclonal antibodies. In addition to intact immunoglobulin molecules, also included in the term "antibody," are fragments or polymers of those immunoglobulin molecules, and human or humanized versions of immunoglobulin molecules or fragments thereof that include the antigen-binding site. These include Fab and F(ab')$_2$ fragments which lack the Fc fragment of an intact antibody.

As used herein, the term "reference levels" refers to the normalized activities and/or levels of a biomarker of interest. For example, normalized enzymatic activities and/or protein levels of neutrophil elastase and proteinase 3 determined from a population of one or more reference subjects that do not have autoimmune diabetes are reference levels for neutrophil elastase and proteinase 3, respectively.

As used herein, "positive reference levels" refer to the normalized activities and/or levels of a biomarker of interest. For example, normalized enzymatic activities and/or protein levels of neutrophil elastase and proteinase 3 determined from a population of one or more subjects that have autoimmune diabetes are positive reference levels for neutrophil elastase and proteinase 3, respectively.

As used herein, the term "level" refers to both an amount of a substance or thing and to the concentration of a substance or thing, as the context indicates.

As used herein, the term "individual", "host", "subject", and "patient" are used interchangeably, and refer to a mammal, including, but are not limited to, murines, simians, humans, mammalian farm animals, mammalian sport animals, and mammalian pets. The term "control," when used in the context of an individual, host, subject, or patient refers to a mammal, including, but are not limited to, murines, simians, humans, mammalian farm animals, mammalian sport animals, and mammalian pets serving as an experimental or comparative control.

As used herein, the term "indicator value" refers to a level or measurement of a parameter, such as a biomarker, that is correlated with or indicative of a state or condition of interest. It is not required that the value of a single parameter be indicative of the state or condition so long as the parameter can contribute to indication of the state or condition.

It is to be understood that the disclosed methods and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. These concepts apply to all aspects of this application including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

Biomarkers for Autoimmune Diabetes

Neutrophil elastase (NE, EC number: 3.4.21.37, encoded by ELA2) and proteinase 3 (PR3, EC number: 3.4.21.76, encoded by PRTN3) are two serine proteases of the chymotrypsin family that are stored in the primary (also known as azurophilic) granules of neutrophils, a type of polymorphonuclear leukocytes (Korkmaz et al., *Pharmacological Reviews* 62:726-759 (2010); Meyer-Hoffert and Wiedow, *Current opinion in hematology* 18:19-24 (2011)). Neutrophils are the most abundant members of the leukocyte population, comprising 40-75% of circulating leukocytes in normal healthy persons, and the first type of leukocytes to be recruited to the site of infection or inflammation where neutrophils can eliminate pathogens by multiple means (Kolaczkowska and Kubes, *Nat Rev Immunol* 13:159-175 (2013); Mestas and Hughes, *Journal of immunology* 172: 2731-2738 (2004)). Traditionally, neutrophils have been well recognized as the major players providing the first line of innate immune defense against infectious disease through oxidative and non-oxidative mechanisms (Mantovani et al., *Nat Rev Immunol* 11:519-531 (2011)). However, increasing evidence suggests that neutrophils are not only the professional killers, but also the major moderators of the immune system in the context of infection and inflammatory disease (Amulic et al., *Annual review of immunology* 30:459-489 (2012)). Neutrophil activation and degranulation result in the release of serine proteases into the extracellular medium and circulation, where they not only help to eliminate the invaded pathogens but also serve as the humoral regulators of the immune responses during acute and chronic inflammation, modulating cellular signaling network by processing chemokines and activating specific cell surface receptors (Meyer-Hoffert and Wiedow, (2011); Pham, *Int J Biochem Cell Biol* 40:1317-1333 (2008); Wiedow and Meyer-Hoffert, *Journal of Internal Medicine* 257:319-328 (2005)). Augmented activities of neutrophil serine proteases have been implicated in the pathogenesis of several inflammatory and autoimmune diseases, including chronic obstructive pulmonary disease, cystic fibrosis, Wegener granulomatosis, Papillion-Lefévre syndrome and small-vessel vasculitis (Korkmaz et al., 2010). However, their association with autoimmune diabetes has not been explored.

Kits

The materials described above, as well as other materials, can be packaged together in any suitable combination as a kit useful for performing, or aiding in the performance of, the disclosed methods. It is useful if the kit components are designed and adapted for use together in the disclosed methods. For example disclosed are kits for measuring the enzymatic activities and/or protein levels of neutrophil elastase and proteinase 3, the kits comprising substrates for neutrophil elastase and proteinase 3.

Kits can include antibodies against neutrophil elastase, proteinase 3, or both. Kits can also include antibodies reactive to the NE and/or PR3 antibodies. These secondary antibodies can be conjugated to a detection enzyme, such as horseradish peroxidase. The kits can also include chromogenic substrates. For example, a chromogenic substrate for the secondary antibody can be included. Kits can also include a chromogenic substrate for measuring the enzymatic activity of neutrophil elastase and proteinase 3.

Mixtures

Disclosed are mixtures formed by performing or preparing to perform the disclosed methods. For example, disclosed are mixtures comprising samples and substrates.

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

Methods for Assessing the Propensity for or Diagnosing Autoimmune Diabetes

In one aspect of the present invention, methods for assessing the risk or propensity to develop and/or the progression of autoimmune diabetes in subjects are provided. The methods comprise determining the enzymatic activities and/or protein concentrations of at least one of neutrophil elastase and proteinase 3 in a subject and comparing the measured enzymatic activities and/or protein concentrations to their respective reference levels. Typically a sample is taken from a subject and the enzymatic activities and/or protein concentrations are measured. The sample can be, e.g., blood, serum, plasma, urine, saliva, cerebrospinal fluid, tears, tissues or combinations thereof. If the enzymatic activities and/or protein concentrations of at least one of neutrophil elastase and proteinase 3 is higher than the corresponding reference levels, the risk or propensity of developing autoimmune diabetes is greater for the subject (e.g., a patient) than a person having the enzymatic activities and/or protein concentrations of at least one of neutrophil elastase and proteinase 3 that is lower than the corresponding reference levels.

In certain embodiments, the reference levels for the enzymatic activities and/or protein concentrations of neutrophil elastase and proteinase 3 can be obtained from one or more subjects that do not have autoimmune diabetes. If the levels for the enzymatic activities and/or protein concentrations of neutrophil elastase and proteinase 3 in the sample are within a statistically acceptable range, for example plus or minus about 10% of the reference levels, then it is indicative of no autoimmune diabetes in the subject; however, if the levels for the enzymatic activities and/or protein concentrations of neutrophil elastase and proteinase 3 in the sample are greater than about 20% above the reference levels, it is indicative of autoimmune diabetes in the subject.

Based on the invention described herein, subjects can be identified, diagnosed, categorized, etc. as at risk of developing an autoimmune diabetes when the enzymatic activities and/or protein levels of at least one of neutrophil elastase and proteinase 3 contained in the sample is above the reference levels of enzymatic activities and/or protein levels of at least one of neutrophil elastase and proteinase 3 obtained from one or more reference subjects that do not have autoimmune diabetes. For example, subjects can be identified, diagnosed, categorized, etc. as at risk of developing autoimmune diabetes when the enzymatic activities and/or protein levels of at least one of neutrophil elastase and proteinase 3 contained in the sample is greater than about 20%, 25%, 30%, 35%, 40%, 45%, 50%, 55%, 60%, 65%, 70%, or more above the respective reference levels of enzymatic activities and/or protein levels of at least one of neutrophil elastase and proteinase 3 obtained from one or more reference subjects that do not have autoimmune diabetes.

Subjects can be identified, diagnosed, categorized, etc. as at risk of developing an autoimmune diabetes when the enzymatic activities and/or protein levels of at least one of neutrophil elastase and proteinase 3 contained in the sample are at least about 20%, 25%, 30%, 35%, 40%, 45%, 50%, 55%, 60%, 65%, or 70% above the respective reference levels of enzymatic activities and/or protein levels of at least one of neutrophil elastase and proteinase 3 obtained from one or more reference subjects that do not have autoimmune diabetes.

In some embodiments, subjects can be identified, diagnosed, categorized, etc. as at risk of developing an autoimmune diabetes when the enzymatic activities of at least one of neutrophil elastase and proteinase 3 contained in the sample are greater than about 40%, 45%, 50%, 55%, 60%, 65%, 70%, 75%, 80%, 85%, 90%, 95%, 100%, or more above the respective reference levels of enzymatic activities of at least one of neutrophil elastase and proteinase 3 obtained from a reference subject that does not have autoimmune diabetes. In some embodiments, a subject can be identified, diagnosed, categorized, etc. as at risk of developing an autoimmune diabetes when the enzymatic activities of at least one of neutrophil elastase and proteinase 3 contained in the sample are at least about 40%, 45%, 50%, 55%, 60%, 65%, 70%, 75%, 80%, 85%, 90%, 95%, or 100% above the respective reference levels of enzymatic activities of at least one of neutrophil elastase and proteinase 3 obtained from one or more reference subjects that do not have autoimmune diabetes.

In some embodiments, subjects can be identified, diagnosed, categorized, etc. as at risk of developing an autoimmune diabetes when the protein levels of at least one of neutrophil elastase and proteinase 3 contained in the sample are greater than about 40%, 45%, 50%, 55%, 60%, 65%, 70%, 75%, 80%, 85%, 90%, 95%, 100%, or more above the respective reference levels of protein levels of at least one of neutrophil elastase and proteinase 3 obtained from a reference subject that does not have autoimmune diabetes. In some embodiments, a subject can be identified, diagnosed, categorized, etc. as at risk of developing an autoimmune diabetes when the protein levels of at least one of neutrophil elastase and proteinase 3 contained in the sample are at least about 40%, 45%, 50%, 55%, 60%, 65%, 70%, 75%, 80%, 85%, 90%, 95%, or 100% above the respective reference levels of protein levels of at least one of neutrophil elastase and proteinase 3 obtained from one or more reference subjects that do not have autoimmune diabetes.

In some embodiments, subjects can be identified, diagnosed, categorized, etc. as at risk of developing an autoimmune diabetes when the protein levels of neutrophil elastase contained in the sample are greater than about 40%, 45%, 50%, 55%, 60%, 65%, 70%, 75%, 80%, 85%, 90%, 95%, 100%, or more above the reference levels of protein levels of neutrophil elastase obtained from one or more reference subjects that do not have autoimmune diabetes. In some embodiments, a subject can be identified, diagnosed, categorized, etc. as at risk of developing an autoimmune diabetes when the protein levels of neutrophil elastase contained in the sample are at least about 40%, 45%, 50%, 55%, 60%, 65%, 70%, 75%, 80%, 85%, 90%, 95%, or 100% above the reference levels of protein levels of neutrophil elastase obtained from one or more reference subjects that do not have autoimmune diabetes.

In some embodiments, a subject can be identified, diagnosed, categorized, etc. as at risk of developing an autoimmune diabetes when the protein levels of proteinase 3 contained in the sample are greater than about 20%, 25%, 30%, 35%, 40%, 45%, 50%, 55%, 60%, 65%, 70%, or more above the reference levels of protein levels of proteinase 3 obtained from one or more reference subjects that do not have autoimmune diabetes. In some embodiments, a subject can be identified, diagnosed, categorized, etc. as at risk of developing an autoimmune diabetes when the protein levels of proteinase 3 contained in the sample are at least about 20%, 25%, 30%, 35%, 40%, 45%, 50%, 55%, 60%, 65%, or 70% above the reference levels of protein levels of proteinase 3 obtained from one or more reference subjects that do not have autoimmune diabetes.

In some embodiments, subjects can be identified, diagnosed, categorized, etc. as at risk of developing an autoimmune diabetes when the enzymatic activity levels of neutrophil elastase contained in the sample are greater than about 40%, 45%, 50%, 55%, 60%, 65%, 70%, 75%, 80%, 85%, 90%, 95%, 100%, or more above the reference levels of enzymatic activities of neutrophil elastase obtained from one or more reference subjects that do not have autoimmune diabetes. In some embodiments, a subject can be identified, diagnosed, categorized, etc. as at risk of developing an autoimmune diabetes when the enzymatic activity levels of neutrophil elastase contained in the sample are at least about 40%, 45%, 50%, 55%, 60%, 65%, 70%, 75%, 80%, 85%, 90%, 95%, or 100% above the reference levels of enzymatic activities of neutrophil elastase obtained from one or more reference subjects that do not have autoimmune diabetes.

In some embodiments, subjects can be identified, diagnosed, categorized, etc. as at risk of developing an autoimmune diabetes when the enzymatic activity levels of proteinase 3 contained in the sample are greater than about 40%, 45%, 50%, 55%, 60%, 65%, 70%, 75%, 80%, 85%, 90%, 95%, 100%, or more above the reference levels of enzymatic activities of proteinase 3 obtained from one or more reference subjects that do not have autoimmune diabetes. In some embodiments, a subject can be identified, diagnosed, categorized, etc. as at risk of developing an autoimmune diabetes when the enzymatic activity levels of proteinase 3 contained in the sample are at least about 40%, 45%, 50%, 55%, 60%, 65%, 70%, 75%, 80%, 85%, 90%, 95%, or 100% above the reference levels of enzymatic activities of proteinase 3 obtained from one or more reference subjects that do not have autoimmune diabetes.

The reference levels of enzymatic activities and/or protein levels of neutrophil elastase and proteinase 3 obtained from one or more reference subjects that do not have autoimmune diabetes can be determined along with the assessment of a subject being tested for risk of autoimmune diabetes or, preferably, by establishing such reference levels to be used with future assays. As disclosed herein, examples of such reference levels are protein levels of neutrophil elastase of 400 ng/mL (or a range of 262 ng/ml to 469 ng/mL), protein levels of proteinase 3 of 100 ng/mL (or a range of 92 ng/mL to 165 ng/mL), and circulating NE/PR3 enzymatic activities of 0.15 mU/mL (or a range of 0.10 mU/mL to 0.21 mU/mL).

The disclosed methods can also be used to identify subjects showing signs of adult onset diabetes, diagnosed with insulin resistance or diagnosed with type 2 diabetes, as being at risk of developing autoimmune diabetes (LADA). A portion of those at risk for developing, or having type 2 diabetes will develop autoimmune diabetes. For these subjects, traditional treatments for type 2 diabetes will fail or will not prevent development of autoimmune diabetes. The disclosed methods can be used to identify such subjects at risk of developing autoimmune diabetes. Once identified, such a subject can receive treatment based on their risk of developing autoimmune diabetes.

The disclosed methods are particularly useful for screening subjects having known risk factors for autoimmune diabetes. Such risk factors include having close family members diagnosed with autoimmune diabetes, having genetic markers of autoimmune diabetes, and having one or more autoimmune diabetes-related autoantibodies. The disclosed methods can provide the earliest indication that subjects are at risk of or are developing autoimmune antibodies. Such early identification can allow earlier, and likely more successful, intervention.

The enzymatic activities of neutrophil elastase and proteinase 3 can be measured using continuous or discontinuous assays by monitoring the change in the absorbance, emission, release or production of light, fluorescence or heat from either substrates or products. In a preferred embodiment, the enzymatic activities of neutrophil elastase and proteinase 3 can be measured using continuous assays by monitoring the change in the absorbance or emission of light or fluorescence from substrates, for example using the synthetic peptide substrates conjugated to a chromogenic or fluoreogenic group, which is released after cleavage. It will be appreciated that any methods of measuring the enzymatic activities of neutrophil elastase and proteinase 3 in a sample can be used. Representative techniques include, but are not limited to, continuous assays by monitoring the color or fluoreogenic generation from the synthetic peptide substrates conjugated to a chromogenic group, such as p-nitroaniline or fluoreogenic group, such as ortho-aminobenzoyl, during the reaction progress.

The protein concentrations of neutrophil elastase and proteinase 3 can be determined using conventional methods such as fluorescence-activated cell sorting (FACS), liquid chromatography/tandem mass spectrometry (LC/MS/MS), surface plasmon resonance (SPR), electrochemical immunoassay, enzyme-linked immunosorbent assay (ELISA), immunohistochemistry or Western blotting. In a preferred embodiment, the protein concentrations of neutrophil elastase and proteinase 3 can be determined using immunological assays, for example ELISA assays or sandwich assays. It will be appreciated that any techniques of quantifying the protein concentrations of neutrophil elastase and proteinase 3 in a sample can be used. Representative methods include, but are not limited to, immunoprecipitation, mass spectroscopy, electrophoresis, and chromatography including affinity chromatography.

Provided herein are assays that can be used, for example, to detect neutrophil elastase (NE) and proteinase 3 (PR3) for use in the methods disclosed herein. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed cancer samples) with an antibody to the molecule of interest or contacting an antibody to a molecule of interest (such as antibodies to NE and PR3) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed NE and PR3 or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

Immunoassays that involve the detection of a substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

An immunoassay that uses electrophoresis that can be used with the disclosed methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., *Protein Methods* (2d edition 1996) and E. Harlow & D. Lane, *Antibodies, a Laboratory Manual* (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Fan Assay, Precipitin Assay, Radioimmune Precipitin Assay; Radioimmunoprecipitation Analysis; Radioimmunoprecipitation Analysis, and Radioimmunoprecipitation Analysis.

Also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}$I or $^{131}$I are often used) with antibody to that antigen. The antibody is generally linked to a solid support, such as a tube or beads. Unlabeled or "cold" antigen is then added in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. For descriptions of ELISA procedures, see Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209-259; Butler, J. E., In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991); Crowther, "ELISA: Theory and Practice," In: Methods in Molecule Biology, Vol. 42, Humana Press; New Jersey, 1995; U.S. Pat. No. 4,376,110, each of which is incorporated herein by reference in its entirety and specifically for teachings regarding ELISA methods.

Variations of ELISA techniques are known to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISAs, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunocomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunocomplex (antigen/antibody) formation. Detection of the immunocomplex then requires a labeled secondary binding agent or a secondary binding agent in conjunction with a labeled third binding agent.

Conditions effective to allow immunocomplex (antigen/antibody) formation refers to conditions that include, for example, diluting the antigens and antibodies with solutions such as BSA, bovine gamma globulin (BGG) and phosphate buffered saline (PBS)/Tween so as to reduce non-specific binding and to promote a reasonable signal to noise ratio.

Effective or suitable conditions generally also include that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunocomplexes between the test sample and the originally bound material, and subsequent washing, the occurrence of even minute amounts of immunocomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunocomplex with a labeled antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data in a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents—which are usually antibodies but can also be alternative protein scaffolds, peptides or nucleic acid aptamers—can be used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays can be used to quantitate and compare the levels of proteins in different samples in health and disease, i.e. protein expression profiling. Proteins other than specific ligand binders can be used in the array format for in vitro functional interaction screens such as protein-protein, protein-DNA, protein-drug, receptor-ligand, enzyme-substrate, etc. The capture reagents themselves can be selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g., where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialized chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include color coding for microbeads (Luminex, Austin, Tex.; Bio-Rad Laboratories) and semiconductor nanocrystals (e.g., QDots™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Fluorescence labeling and detection methods are widely used and can be used with the disclosed methods. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in E. coli, after selection from phage or ribosome display libraries (Cambridge Antibody Technology, Cambridge, UK; BioInvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staph. aureus* protein A (Affibody, Bromma, Sweden), 'Trinectins' based on fibronectins (Phylos, Lexington, Mass.) and 'Anticalins' based on the lipocalin structure (Pieris Proteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labeling is used for comparison of different samples with different colors. Where pairs of antibodies directed at the same protein ligand are available, sandwich immunoassays provide high specificity and sensitivity and are therefore the method of choice for low abundance proteins such as cytokines; they also give the possibility of detection of protein modifications.

Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Assays for determining enzymatic activities of neutrophil elastase and proteinase 3 are also described. Chromogenic assays are preferred. Chromogenic enzymatic assays use chromogenic substrates for the enzyme to be assayed. Such chromogenic substrates are cleaved or otherwise reacted by the enzyme to produce a detectable product. The detectable product can be colored, can have a specific absorption or emission spectrum, can be fluorescent, luminescent, or otherwise produce a detectable electromagnetic signal. An example of a useful chromogenic substrate for NE/PR3 activity measurement is MeOSuc-Ala-Ala-Pro-Val-pNA (cleavage of p-nitroaniline (pNA) from the substrate increases absorbance at 405 nm).

Another method aspect of the present invention for diagnosing or aiding in the diagnosis of autoimmune diabetes in a subject includes obtaining a sample from the subject, preferably a blood sample, and determining the enzymatic activities and/or protein concentrations of neutrophil elastase and proteinase 3 contained in the sample. The determined levels are compared to the reference levels. In a preferred embodiment, autoimmune diabetes is present if the enzymatic activities and/or protein concentrations of neutrophil elastase and proteinase 3 are higher than the reference levels. In another preferred embodiment, the enzymatic activities of neutrophil elastase and proteinase 3 in the blood sample are measured using continuous assays by monitoring the color or fluoreogenic generation during the reaction progress, preferably monitoring the color generation from the synthetic peptide substrates conjugated to p-nitroaniline during the reaction progress. The protein concentrations of neutrophil elastase and proteinase 3 in the blood sample are determined using an immunoassay, preferably a sandwich immunoassay. The results of these methods can be used in combination with other tests to diagnose autoimmune diabetes in a subject. For example, levels of blood glucose, glycated hemoglobin, C-peptide or the presence of islet-specific autoantibodies can be measured. The data combined with the determining the enzymatic activities and/or protein concentrations of neutrophil elastase and proteinase 3 can be used to assess the risk of developing or diagnosis the presence of autoimmune diabetes.

Treating to Reduce Risk of Developing an Autoimmune Diabetes

In various aspects of the present invention, reducing the risk of or preventing onset of autoimmune diabetes can be accomplished by any of the strategies and techniques designed for treatment or prevention of type 1 diabetes. Most strategies involve affecting the immune system to reduce or prevent further development of type 1 diabetes.

For example, environmental triggers of islet autoimmunity such as cow's milk or gluten can be avoided. Celiac disease provides an encouraging example of autoimmune disease that can be prevented in this way. Alternatively, diet can be supplemented with nutrients for which deficiency presumably promotes islet autoimmunity, e.g., n-3 fatty acids or vitamin D. Antigen-specific "vaccination" using islet autoantigens, for example, intact insulin, altered insulin or proinsulin peptides, $GAD_{65}$, or heat shock protein 60 (HSP60) peptide. (Ludvigsson et al. New Engl J Med 359:1909-1920 (2008). The goal is to induce autoantigen-specific tolerance by induction of regulatory T-cells that downregulate immunity to a specific autoantigen as well as promote tolerance to additional autoantigens. Non-antigen-specific systemic therapies that range from mild modulation with oral nicotinamide or bacille Calmette-Guerin (BCG) vaccination to immunosuppression and cellular therapies can also be used. Stimulation of β-cell regeneration in conjunction with suppression of apoptosis that is increased in islet autoimmunity to overcome the relapsing-remitting course of pre-diabetes is another strategy that can be used. Metabolic modifications, such as weight loss and maintenance, increased physical activity, and β-cell rest are other examples.

Other examples include antagonizing B-cell activating factor (BAFF) (Marino et al. *Diabetes* 61(11):2893-2905 (2012)), promote expression of diabetes-resistant MHC class II molecules (Tian et al., J. Clin. Invest. 114(7):969-978 (2004)), CD3 activation (Herold et al. Diabetes. 62(11): 3766-3774 (2013); Herold et al., New Engl J Med 346(22): 1692-1698 (2002) (OKT3 antibody)), anti-thymocyte globulin (ATG) therapy (Gitelman et al., The Lancet Diabetes & Endocrinology 1(4):306-316 (2013); Eisenbarth et al. Diabetes Res 2:271-276 (1985)), Treg therapy (Du et al., PLoS One 8(2):e56209 (2013)), CTLA-4 inhibition, tumor necrosis factor-α (Mastrandrea et al. Diabetes Care 32:1244-1249 (2009)), IL-1 receptor antagonist, pegylated granulocyte colony-stimulating factor, human recombinant interferon-α (Rother et al. Diabetes Care 32:1250-1255 (2009)), autologous stem cell transplantation (Haller et al. Diabetes 58(Supp. 1):A7 (2009) (Abstract); Voltarelli et al. Ann NY Acad Sci 1150:220-229 (2008); Voltarelli et al. JAMA 297:1568-1576 (2007); Couri et al., JAMA 301:1573-1579 (2009)). Because neutrophils play a role in the attack on β-cells, neutrophil depletion and/or inhibition can be used. Neutrophils can be depleted by the use of Ly6G-specific antibodies. Daley et al., J. Leukocyte Biol. 83:64-69 (2008). Neutrophil activity can be reduced by blocking or antagonizing Ly6G. Wang et al., Blood 120(7):1489-1498 (2012).

These and other techniques for reducing the risk of or preventing onset of an autoimmune diabetes are described in U.S. Patent Application Publication Nos. 2014/0045923, 2013/0345257, 2013/0338039, 2013/0280208, 2013/0164302, 2013/0109107, 2012/0225131, 2012/0003240, 2012/0003239, 2012/0003238, 2011/0236370, 2011/0200610, 2011/0124609, 2011/0111023, 2010/0166669, 2010/0143374, 2010/0047273, 2010/0028450, 2009/0305340, 2009/0252753, 2009/0226440, 2009/0092637, 2008/0248055, 2008/0187522, 2006/0240032, 2006/0115899, and 2005/0271641.

Additional methods, provided by aspects of the present invention, for prevention or reducing the risk of autoimmune diabetes include the use of chemical or peptide inhibitors of NE and/or PR3 for blocking the enzymatic activities (Groutas et al., Expert Opinion on Therapeutic Patents 21(3):339-354 (2011); Crocetti et al., J. Med. Chem. 56(15):6259-6272 (2013)), or any compound that can block the neutrophil activation. Examples include α1-protease inhibitor, 3,4 dichloroisocoumarin, soybean trypsin inhibitor, elastatinal, N-(methylsuccinyl)-Ala-Ala-Pro-Val-chloromethyl ketone, sivelestat, SSR 69071, AZD9668, ONO-6818, elafin, anti-neutrophil cytoplasmic antibodies (ANCA), antibodies to NE, and antibodies to PR3.

Actions Based on Identifications

Embodiments of the methods of the present invention include the determination, identification, indication, correlation, diagnosis, prognosis, etc. (which can be referred to collectively as "identifications") of subjects, diseases, conditions, states, etc. based on measurements, detections, comparisons, analyses, assays, screenings, etc. For example, subjects can be identified as at risk of developing autoimmune diabetes. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing, or that could benefit from, the treatment will receive it and subjects that do not need, or would not benefit from, the treatment will not receive it.

Accordingly, embodiments of the methods provided comprise taking particular actions following, and based on, the disclosed identifications. For example, provided are methods comprising creating a record of an identification (in physical—such as paper, electronic, or other—form, for example). Thus, for example, creating a record of an identification based on the methods provided differs physically and tangibly from merely performing a measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc. the subject based on the identification); retained for later use or review; used as data to assess sets of subjects, treatment efficacy, accuracy of identifications based on different measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The methods of creating a record can be combined with any one or more other methods provided, and in particular, with any one or more steps of the methods of identification.

As another example, methods of the present invention comprise making one or more additional identifications based on one or more other identifications. For example, particular treatments, monitorings, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The methods of making a further identification can be combined with any one or more other methods disclosed herein, and in particular, with any one or more steps of the methods of identification.

As another example, methods are provided for treating, monitoring, following-up with, advising, etc. a subject identified in any of the methods provided by the present invention. Also provided are methods comprising treating, monitoring, following-up with, advising, etc. a subject for which a record of an identification from any of the provided methods has been made. For example, particular treatments, monitorings, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The methods of treating, monitoring, following-up with, advising, etc. can be combined with any one or more other methods provided herein, and in particular, with any one or more steps of the methods of identification.

The measurements, detections, comparisons, analyses, assays, screenings, etc. can be used in other ways and for other purposes than those provided herein. For example, identification that a subject diagnosed with diabetes does not have high levels of neutrophil elastase and proteinase 3 can be used to confidently treat the subject for type 2 diabetes by eliminating the possibility that the subject might develop latent autoimmune diabetes in adults. Thus, the provided measurements, detections, comparisons, analyses, assays, screenings, etc. do not encompass all uses of such measurements, detections, comparisons, analyses, assays, screenings, etc.

The term "hit" refers to a test compound that shows desired properties in an assay. The term "test compound" refers to a chemical to be tested by one or more screening method(s) as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100%, compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist".

The term "inhibit" as used herein means to reduce or decrease in activity or expression. This can be a complete inhibition or activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include, for example, the use of pipettes, pipettemen, syringes, needles, tubing, guns, etc. This can be manual or automated. It can include transfection by any means or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

By the term "effective amount" of a compound as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

By the term "infant" is meant a young baby, from birth to 12 months of age. By the term "child" is meant a person who has not yet reached puberty. By the term "adolescent" is meant a person between the onset of puberty and adulthood. By the term "adult" is meant a person who has reached full maturity (generally considered age 18).

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject in need of treatment for autoimmune diabetes or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

Compounds used for treating subjects can be conveniently formulated into pharmaceutical compositions composed of one or more of the compounds in association with a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. These most typically are standard carriers for administration of compositions to humans or non-humans, including solutions such as sterile water, saline, and buffered solutions at physiological pH. Other compounds will be administered according to standard procedures used by those skilled in the art.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Anyone or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By citation of various references in this document, Applicants do not admit any particular reference is "prior art" to their invention.

EXAMPLES

The methods, compounds, and compositions herein described are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. All parts or amounts, unless otherwise specified, are by weight.

Example 1

Antibody Production and Development of Sandwich ELISA for Determining Protein Levels of Human and Murine Neutrophil Elastase and Proteinase 3

The polyclonal antibodies against the recombinant human and murine neutrophil elastase and proteinase 3 were generated in New Zealand female rabbit as described previously (Xu et al., *Proceedings of the National Academy of Sciences of the United States of America* 102:6086-6091 (2005)). The antibodies against human and murine neutrophil elastase and proteinase 3 were purified from the immunized rabbit serum using protein A/G beads, followed by affinity chromatography using their respective antigens as the ligands. The affinity-purified antibodies against human and murine neutrophil elastase and proteinase 3 were biotinylated with a kit from Pierce and used as the detection antibodies. The unlabeled anti-human and anti-murine neutrophil elastase and proteinase 3 were used for coating a 96-well microtiter plate overnight at 4° C.

Human or murine serum was diluted (1:100) into 1× assay diluent (1% BSA in 1×PBS), and 100 μl of the diluted samples or recombinant standards were applied to each well and incubated at 37° C. for 1 hour. The plates were washed three times and then incubated with 100 μl of the detection antibody for another 1 hour at 37° C. After washing for another three times with 1×PBST (1×PBS containing 0.5% Tween-20), the wells were incubated with streptavidin-conjugated horseradish peroxidase for 20 minutes and subsequently reacted with tetramethylbenzidine reagent for 15 minutes. A total of 100 μl of 2 M $H_2SO_4$ was added to each well to stop the reaction.

The limits of detection were 0.156 ng/ml for human and murine neutrophil elastase ELISA as well as human proteinase 3 ELISA, determined by the mean O.D value of 20 replicates of the zero standard added by their three standard deviations. These assays were highly specific to human and murine neutrophil elastase and proteinase 3, respectively, with no detectable cross-reactivity to other human and murine proteins. The intra- and inter-assay coefficients of variance were 3.9-4.5% and 4.3-5.1% respectively, determined by measuring five serum samples in a total of six independent assays with duplicate determinations.

Example 2

Development of Chromogen-Based Assay for Measuring Enzymatic Activities of Human Neutrophil Elastase and Proteinase 3

A synthetic chromogenic substrate methoxysuccinyl-Ala-Ala-Pro-Val-p-nitroaniline (Km=0.28 mM, Kcat/Km=33915 $M^{-1}s^{-1}$ for human neutrophil elastase, Km=1.2 mM, Kcat/Km=499 $M^{-1}s^{-1}$ for human proteinase 3) was used as described previously (Wiesner et al., FEBS Lett 579:5305-5312 (2005)). The substrate was dissolved in N, N-dimethylformamide to make a 10 mmol/L stock (10×) and diluted with 100 mmol/L Tris-HCl buffer (pH 8.0, containing 500 mmol/L NaCl) as the substrate working solution when used. P-nitroaniline standard was dissolved in N, N-dimethylformamide to make a 100 mmol/L stock and diluted with 100 mmol/L Tris-HCl buffer (pH 8.0, containing 500 mmol/L NaCl) to make 0, 100, 200, 300, 400 and 500 μmol/L for generating the standard curve when used.

Human serum (20 μl) was incubated with 180 μl of the substrate working solution at 37° C. for 24 hours. The liberated p-nitroaniline and diluted p-nitroaniline standard were measured spectrophotometrically at 405 nm. The enzymatic activities of neutrophil elastase and proteinase 3 were calculated according to the delta OD values before and after 24-hour incubation with substrate and expressed as mU/ml serum, where one unit was defined as the amount of neutrophil and proteinase 3 that hydrolyze the substrate to yield 1.0 μmol of p-nitroaniline per minute at 37° C.

Example 3

Evaluation of Circulating Protein Levels and Enzymatic Activities of Human Neutrophil Elastase and Proteinase 3 in Subjects with Type 1 Diabetes Human Subjects—

149 subjects with type 1 diabetes (mean age, 14.2±4.8 years; median age, 14.0 years; age range, 4-29 years; 61.7% female) were recruited to the study. Patients with T1D were diagnosed according to American Diabetes Association criteria (American Diabetes Association, 2013) as follows: fasting plasma glucose ≥7.0 mmol/L and/or HbA1C≥6.5%, fasting C-peptide levels <200 pmol/L, ketosis or ketoacidosis at onset, or the presence of at least one islet-specific autoantibody (GADA, IA2A or ZnT8A). All patients were on insulin treatment. Eight had thyroidal autoimmune disorder. The disease duration of T1D was 4.2 (1.7-7.1) [median (interquartile range)].

A control group of 77 age- and sex-matched healthy subjects (mean age, 13.2±5.4 years; median age, 15.0 years; age range, 2-21 years; 44.2% female) were included using the following inclusion criteria: (1) fasting plasma glucose less than 5.6 mmol/L and 2-h plasma glucose less than 7.8 mmol/L; (2) no family history of diabetes, and other autoimmune or chronic diseases.

Clinical and Biochemical Assessments—

After overnight fasting, a venous blood specimen was collected in the morning (around 0800 am) for analysis of various biochemical parameters. Plasma glucose was measured enzymatically on a Hitachi 7170 analyzer (Boehringer Mannheim, Mannheim, Germany). HbA1c was measured by automated liquid chromatography (Bio-Rad VARIANT II Hemoglobin Testing System, Hercules, Calif., USA). Serum levels of C-peptide and C-reactive protein were quantified using a chemiluminescence immunoassay on a Bayer 180SE Automated Chemiluminescence Systems (BayerAG Leverkusen, Germany), and an immunoturbidimetric assay (Orion Diagnostica, Espoo, Finland), respectively. The titers of GADA, IA2A and ZnT8A were determined by the assays as previously described (Xiao et al., *The Journal of clinical endocrinology and metabolism* 97:E54-58 (2012); Yang et al., *Diabetes/metabolism research and reviews* 26:579-584 (2010)).

The levels of neutrophil NETosis were measured by quantifying the amount of circulating MPO-DNA complexes, a well-established marker of NET formation (Kessenbrock et al., *Nat Med* 15:623-625 (2009)). Briefly, 5 μg/ml of mouse anti-MPO monoclonal antibody (ABD Serotec, Germany) was coated to 96-well microtiter plates overnight at 4° C. After blocking with 1% BSA, serum samples were added per well in combination with the peroxidase-labeled anti-DNA monoclonal antibody (component No. 2 of the Cell Death Detection ELISA PLUS kit, Roche Diagnostics, USA) according to the manufacturer's instructions. After two hours of incubation at room temperature on a shaking device (300 rpm), the samples were and the peroxidase substrate was added. The absorbance was measured at 405 nm using a μQuant microplate reader (BioTek, USA).

Statistical Analysis—

All analyses were performed with Statistical Package for Social Sciences version 16.0 (SPSS, Chicago. Ill.). Normality was tested using the Kolmogorov-Smirnov test. Data that were not normally distributed were logarithmically transformed before analysis. Differences between groups were assessed by $\chi^2$ or unpaired t test. Comparisons among groups were performed using one-way ANOVA and independent t-tests. Correlations were analyzed using Pearson correlation or partial correlation as appropriate. Data were expressed as mean±SD or median with interquartile range as appropriate. In all statistical comparisons, a p value <0.05 was used to indicate a statistically significant difference.

Results—

The clinical characteristics of T1D patients and their healthy controls are described in Table 1. Compared with healthy subjects, T1D patients had higher fasting glucose and HbA1c, but lower fasting C-peptide levels. No significant differences in C-reactive protein were found between two groups (Table 1). Consistent with the previous reports (Harsunen et al., *Hormone and metabolic research=Hormon-und Stoffwechselforschung=Hormones* et metabolisme 45:467-470 (2013); Valle et al., *Diabetes* 62:2072-2077 (2013)), the circulating neutrophils were moderately reduced in T1D patients compared with the healthy controls [median (interquartile range) ($\times 10^6$/ml), 3.26 (2.54-4.13) vs 3.63 (3.02-4.15), p<0.05] (Table 1).

The protein levels and enzymatic activities of neutrophil elastase and proteinase 3 in serum samples from these subjects were measured using in-house developed chromogen-based assays as provided in Example 1 and sandwich ELISA kits as provided in Example 2. In contrast to the mild reduction of peripheral neutrophils, the results showed that the circulating protein levels of both NE and PR3 were dramatically increased in T1D patients compared to the healthy controls [NE: 1594.7 (988.4-2284.6) vs 397.0 (262.2-468.8) ng/ml, p<0.001; PR3: 295.3 (206.0-430.4) vs 107.4 (92.5-165.0) ng/ml, p<0.001] (FIGS. 1 (A and B)). The circulating NE/PR3 enzymatic activities in T1D patients were also substantially higher than those in healthy individuals [0.69 (0.41-1.03) vs 0.14 (0.10-0.21) mU/ml, p<0.001] (FIG. 1(C)). The correlation coefficient between NE/PR3 enzymatic activities and circulating protein levels was 0.915 (p<0.001) for NE and 0.874 (p<0.001) for PR3. There were no differences in circulating protein levels and enzymatic activities of NE and PR3 between men and women in patients or controls.

TABLE 1

Characteristics of healthy controls and T1D patients recruited for this study

| | Healthy controls | T1D patients |
|---|---|---|
| n | 77 | 149 |
| Age (years) | 13.3 ± 5.3 | 14.2 ± 4.8 |
| Sex (men/women) | 43/34 | 57/92 |
| BMI (kg/m$^2$) | 18.35 ± 2.70 | 18.04 ± 3.37 |
| Duration of diabetes (years) | N/A | 4.56 ± 3.36 |
| Fasting glucose (mmol/L)$^§$ | 4.69 (4.41-4.89) | 8.40 (6.15-12.65)* |
| HbA1c (%)$^§$ | 5.00 (4.80-5.15) | 7.50 (6.45-9.55)* |
| (mmol/mol)$^§$ | 31 (29-33) | 58 (47-81)* |
| Fasting C-peptide (pmol/L)$^§$ | 445.4 (362.1-678.2) | 15.7 (5.5-72.2)* |
| C reactive protein (mg/L)$^§$ | 0.23 (0.13-0.61) | 0.28 (0.15-0.66) |
| Blood cell counts | | |
| Erythrocytes ($\times 10^6$/ml)$^§$ | 4.66 (4.30-4.94) | 4.80 (4.43-5.04) |
| White blood cells ($\times 10^6$/ml)$^§$ | 6.85 (5.80-7.78) | 5.70 (4.80-6.95)* |
| Lymphocytes ($\times 10^6$/ml)$^§$ | 2.18 (1.55-2.62) | 1.82 (1.57-2.35) |
| Monocytes ($\times 10^6$/ml)$^§$ | 0.42 (0.34-0.49) | 0.29 (0.22-0.36)* |
| Neutrophils ($\times 10^6$/ml)$^§$ | 3.63 (3.02-4.15) | 3.26 (2.54-4.13)* |
| Eosinophils ($\times 10^6$/ml)$^§$ | 0.20 (0.12-0.34) | 0.14 (0.11-0.21)* |
| Basophils ($\times 10^6$/ml)$^§$ | 0.05 (0.03-0.06) | 0.07 (0.04-0.10)* |
| Platelets ($\times 10^6$/ml)$^§$ | 256 (223-315) | 240 (197-279)* |

Data are expressed as mean ±SD or median (interquartile range) as appropriate.
*P < 0.05 compared with healthy controls.
$^§$Log transformed before analysis.

Figure 2:
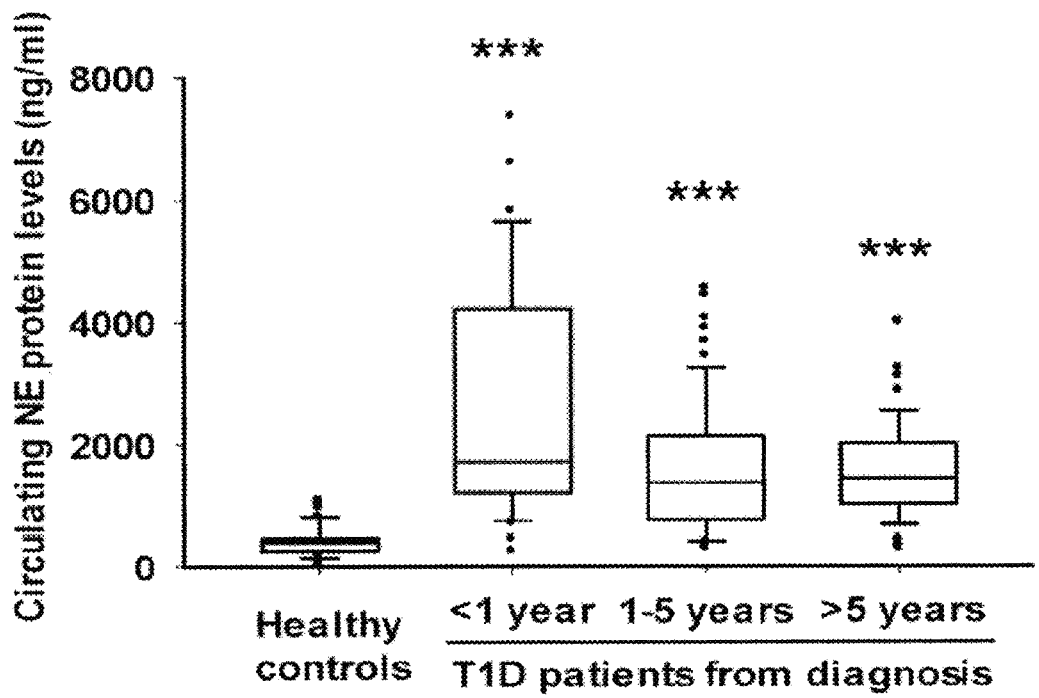
FIG. 2 shows graphs illustrating circulating protein levels of NE (A) and PR3 (B), enzymatic activities of both NE and PR3 (C), neutrophil counts (D) and A1AT (E) in healthy controls (n=77), T1D patients within 1 year from diagnosis (n=28), with a disease duration >1 and <5 years (n=59) and with duration >5 years (n=62). The horizontal line in the middle of each box indicates the median value; the top and bottom borders of the boxes represent the $75^{th}$ and $25^{th}$ percentiles, respectively; the whiskers represent the $10^{th}$ and $90^{th}$ percentiles, and the dots represent the outliers. p<0.01, *p<0.001 vs healthy controls
Figure 2:
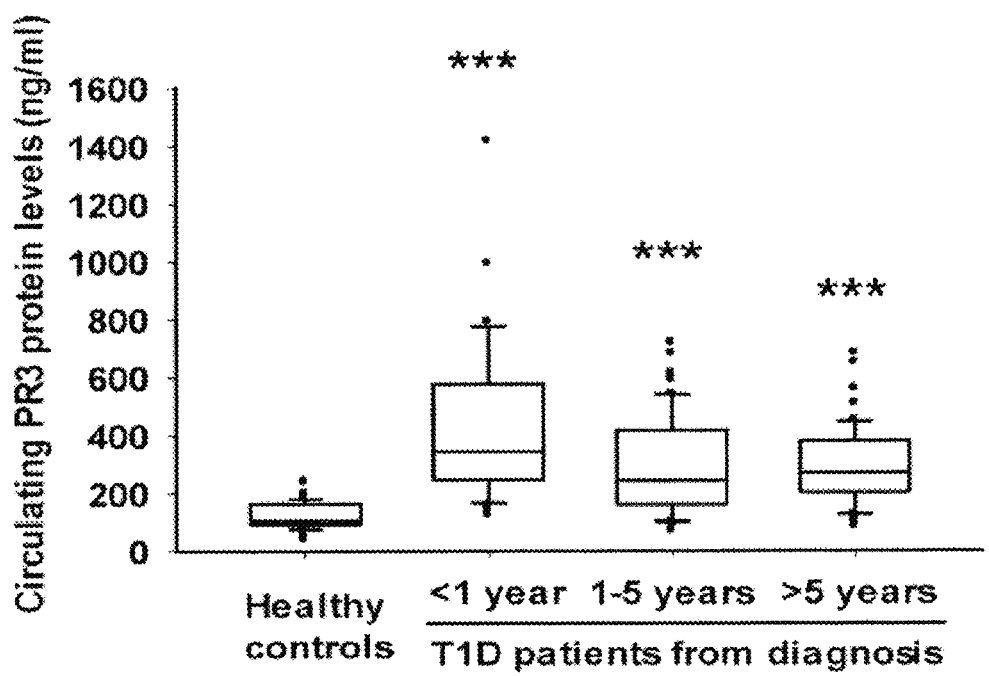
Figure 2:
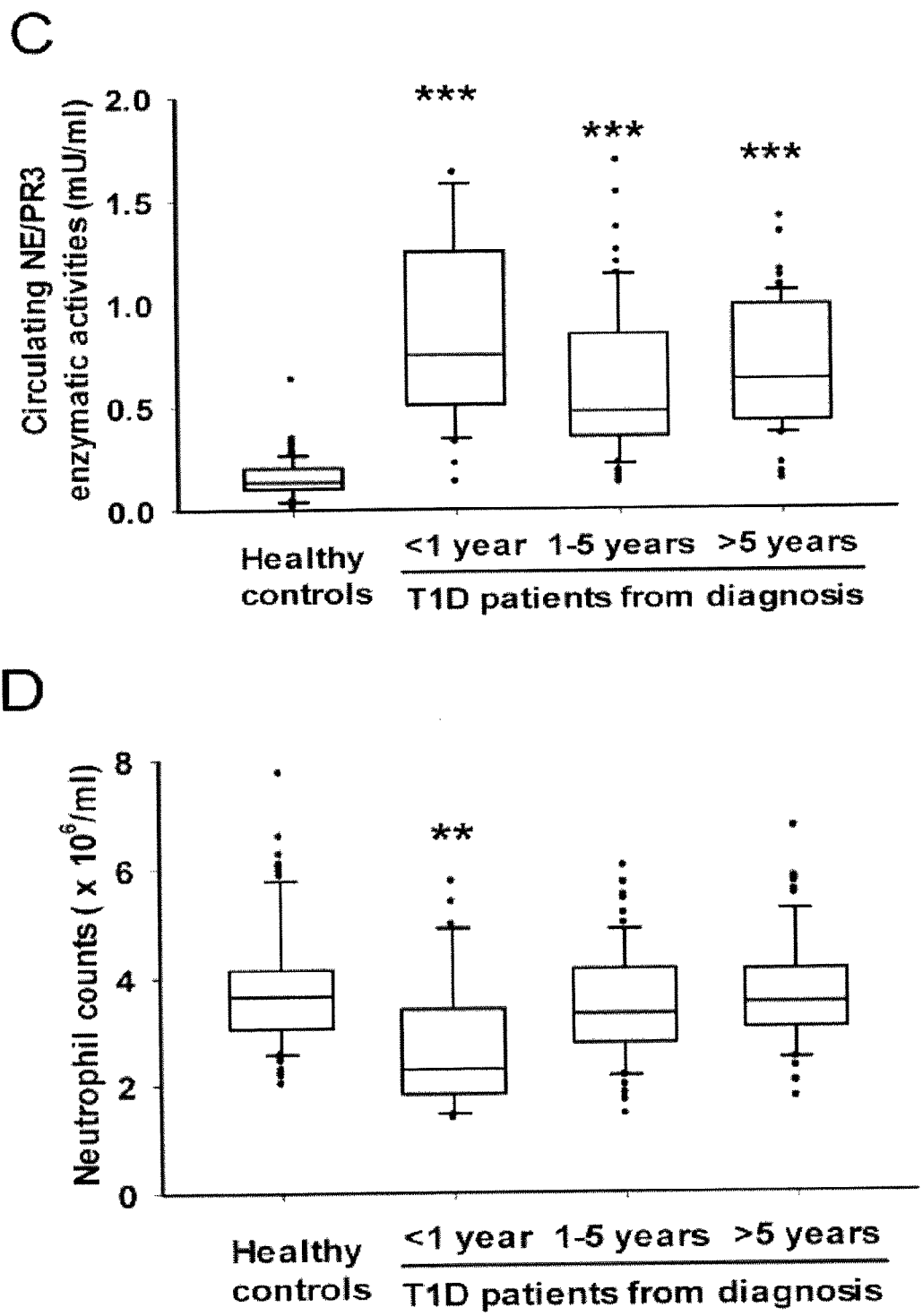
Figure 2:
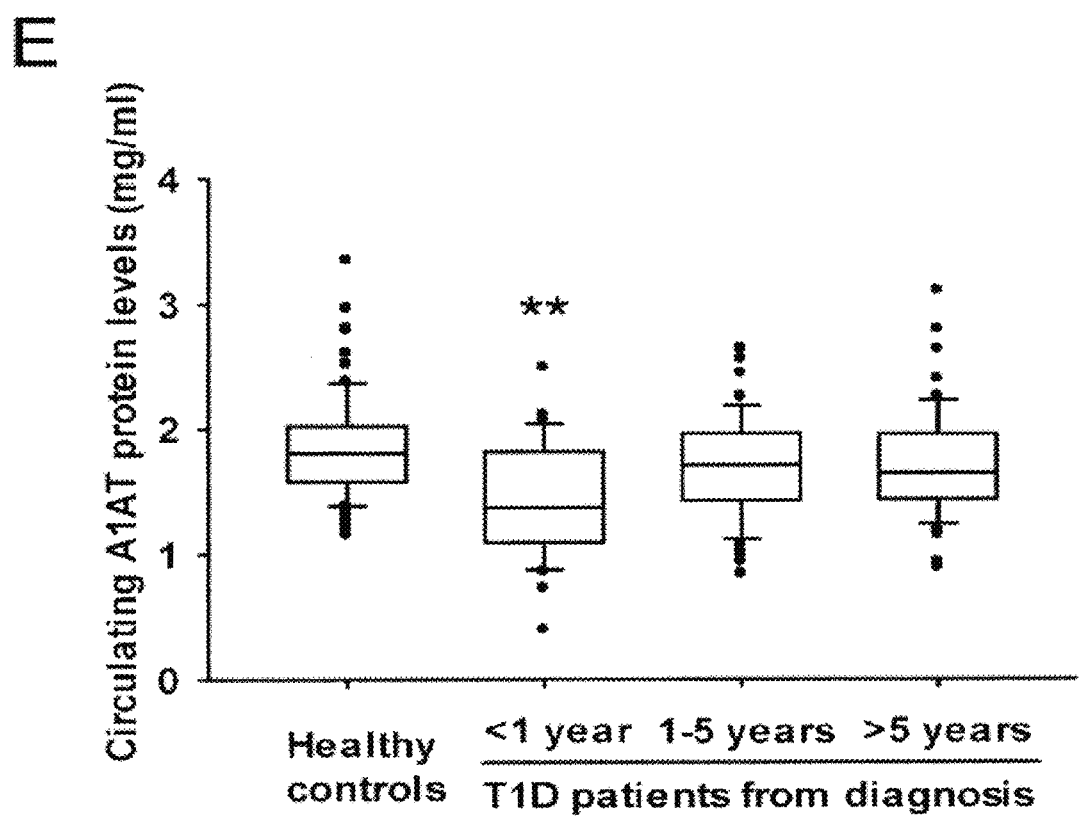

To further analyze the changes of circulating NE and PR3 during the progression of autoimmune diabetes, T1D patients were divided into three groups based on their disease duration, including patients within 1 year from diagnosis (n=28), with a disease duration >1 and <5 years (n=59) and with duration >5 years (n=62). Notably, the magnitude of increases in both protein levels and enzymatic activities of NE and PR3 was significantly higher in T1D patients diagnosed within 1 year as compared to the other two groups of patients with longer disease duration (FIG. 2 (A-C)). On the other hand, a significant reduction in circulating neutrophils was observed only in T1D patients diagnosed within one year, whereas the decline in the other two groups did not reach statistically significance (FIG. 2 (D)).

The activities of plasma NE and PR3 are tightly controlled by their associated endogenous inhibitors, especially A1AT, an archetype member of the serine protease inhibitor (SERPIN) superfamily. In contrast to elevated NE and PR3 levels, the circulating concentrations of A1AT in T1D patients were significantly decreased compared to healthy subjects [1.61 (1.37-1.93) vs 1.80 (1.57-2.07) mg/ml, p<0.01] (FIG. 1 (D)). Further analysis showed that the decline in A1AT levels in patients diagnosed within one year was greater than those with disease duration for 1-5 years and >5 years respectively (FIG. 2 (E)).

Figure 3:
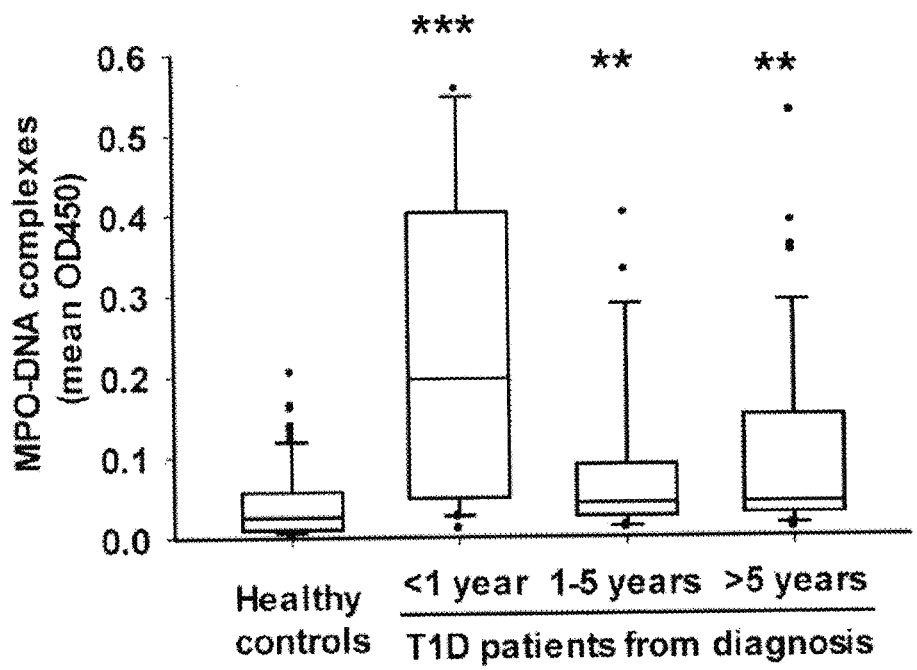
FIG. 3 shows graphs illustrating circulating levels of MPO-DNA complexes in healthy controls (n=77), T1D patients within 1 year from diagnosis (n=28), with a disease duration >1 and <5 years (n=59) and with duration >5 years (n=62) (A). Circulating MPO-DNA complexes were significantly correlated with circulating NE (B) and PR3 (C) protein levels, and enzymatic activities of both NE and PR3 (D).  p<0.01, * p<0.001 vs healthy controls.
Figure 3:
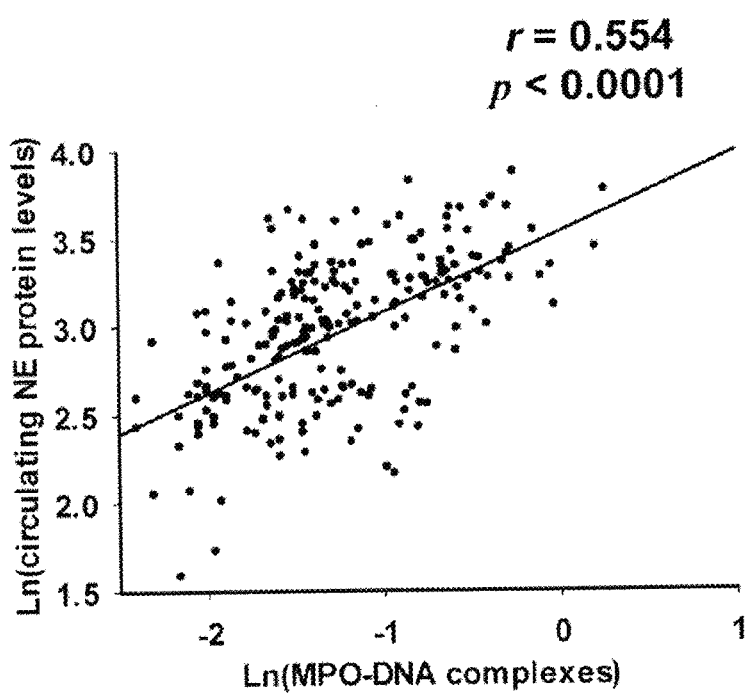
Figure 3:
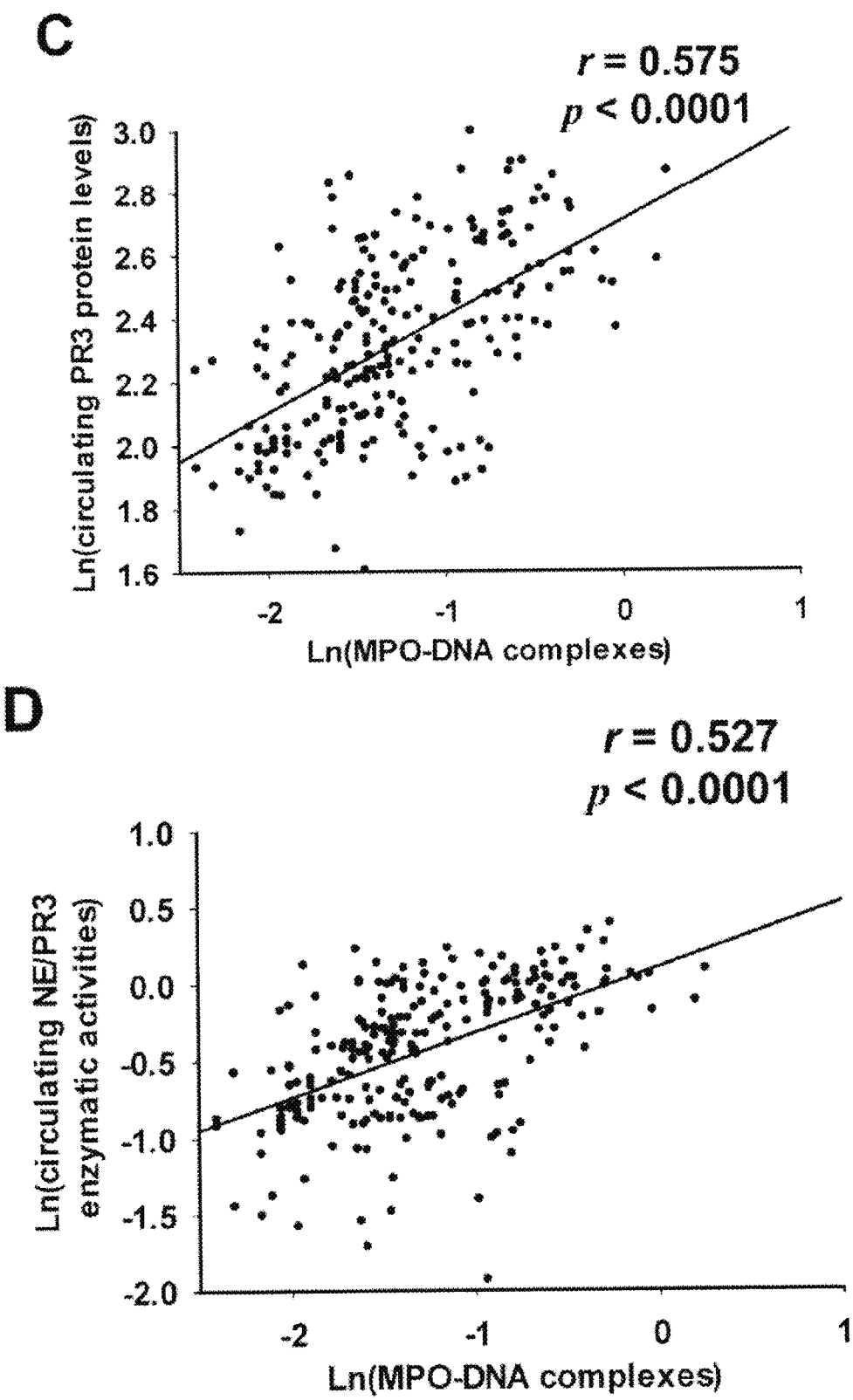

To explore the underlying mechanism responsible for the markedly elevated circulating NE and PR3 levels, the levels of neutrophil NETosis were measured by quantifying the amount of circulating MPO-DNA complexes, a well-established marker of NET formation (Kessenbrock et al., 2009). In line with the increased NE and PR3 levels, a significant elevation of circulating MPO-DNA complexes was observed in T1D patients, especially in T1D patients with the disease duration of less than one year, compared to the healthy individuals [0.197 (0.049-0.412) vs 0.026 (0.011-0.058) (mean OD405), p<0.001] (FIG. 3 (A)). Furthermore, the amount of MPO-DNA complexes in serum was significantly correlated with the circulating protein levels of NE (r=0.554, p<0.001) and PR3 (r=0.575, p<0.001), as well as NE/PR3 enzymatic activities (r=0.527, p<0.001) (FIG. 3 (B-D)), suggesting that the increased circulating NE and PR3 protein levels in T1D patients are at least in part attributed to enhanced neutrophil NETosis.

Figure 4:
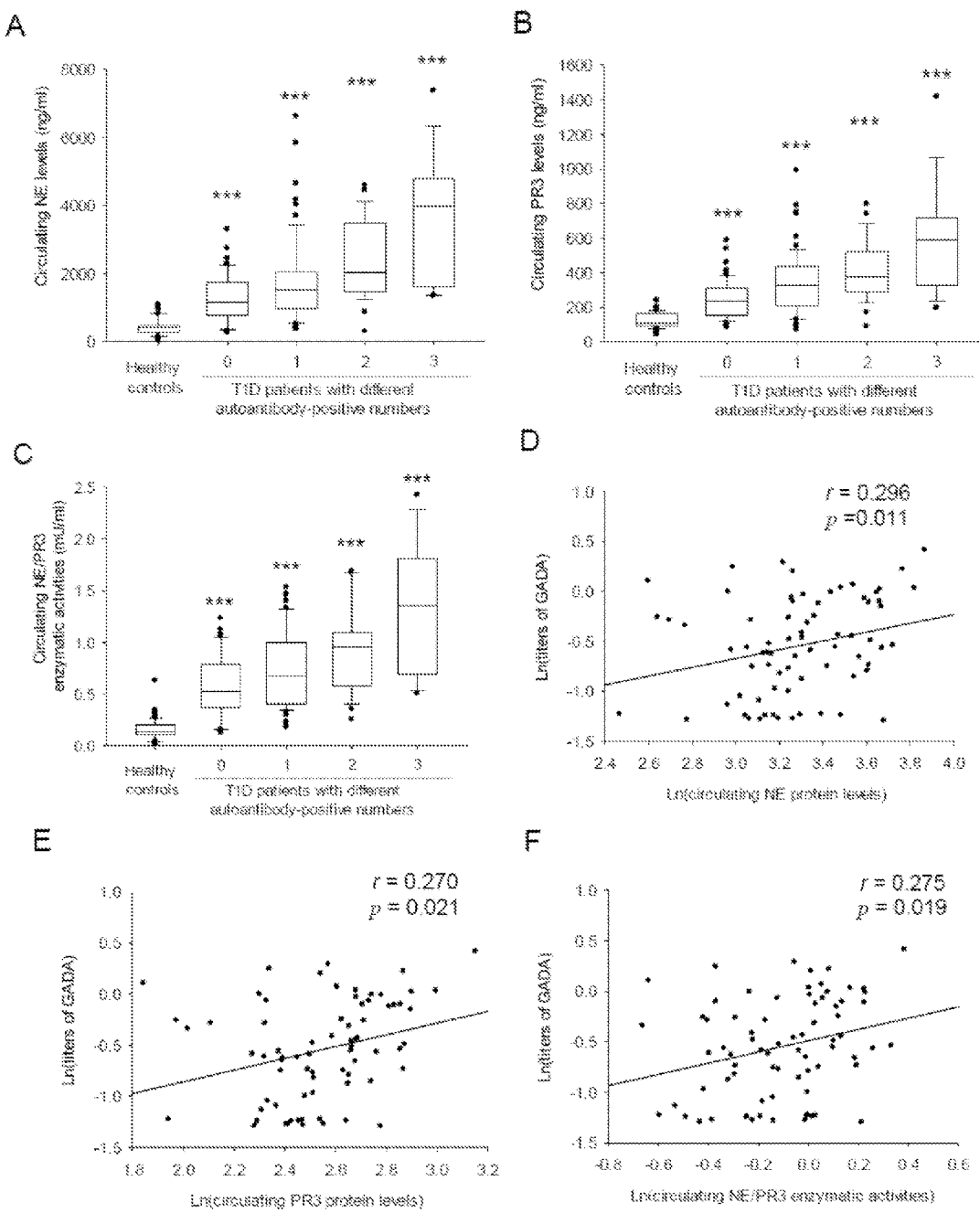
FIG. 4 shows graphs illustrating circulating protein levels of NE (A) and PR3 (B), enzymatic activities of both NE and PR3 (C) in healthy controls (n=77), T1D patients with autoantibody negative (n=54), one autoantibody-positive of GADA, IA2A or ZnT8A (n=61), two autoantibodies-positive of GADA, IA2A or ZnT8A (n=24), or three autoantibodies-positive of GADA, IA2A and ZnT8A (n=10). Circulating protein levels of NE (D) and PR3 (E), and enzymatic activities of both NE and PR3 (F) were significantly correlated with the titers of GADA in T1D patients with GADA-positive (n=73). ***p<0.0001 vs healthy controls.
Figure 5:
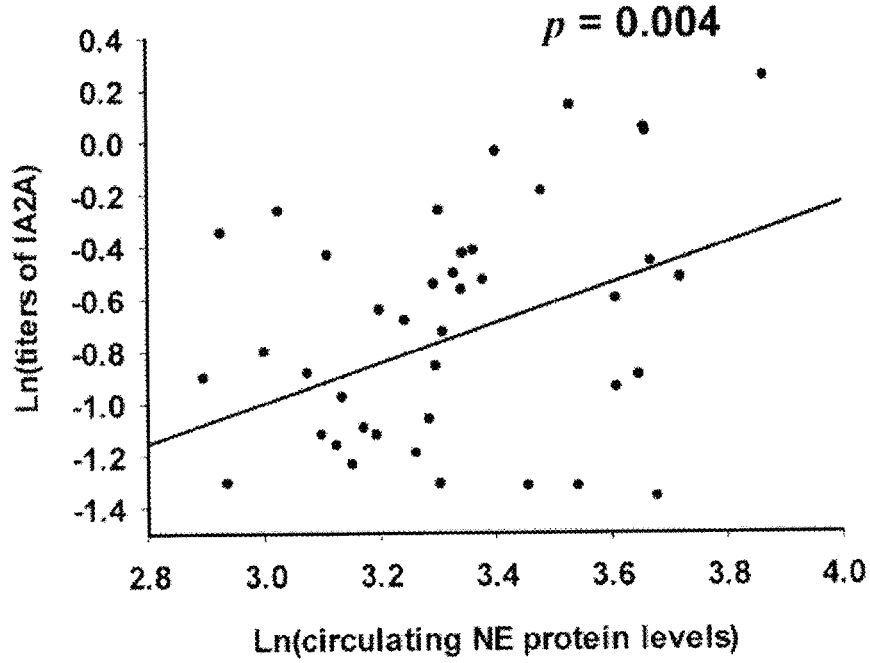
FIG. 5 shows graphs illustrating circulating protein levels of NE (A) and PR3 (B), and enzymatic activities of both NE and PR3 (C) which significantly correlated with the titers of IA2A in T1D patients with IA2A-positive (n=44).
Figure 5:
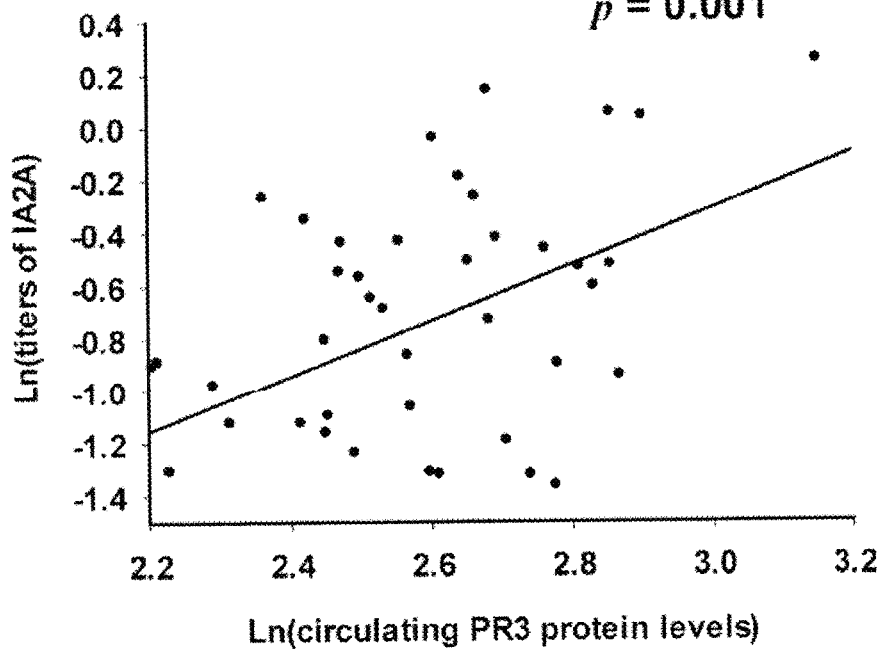
Figure 5:
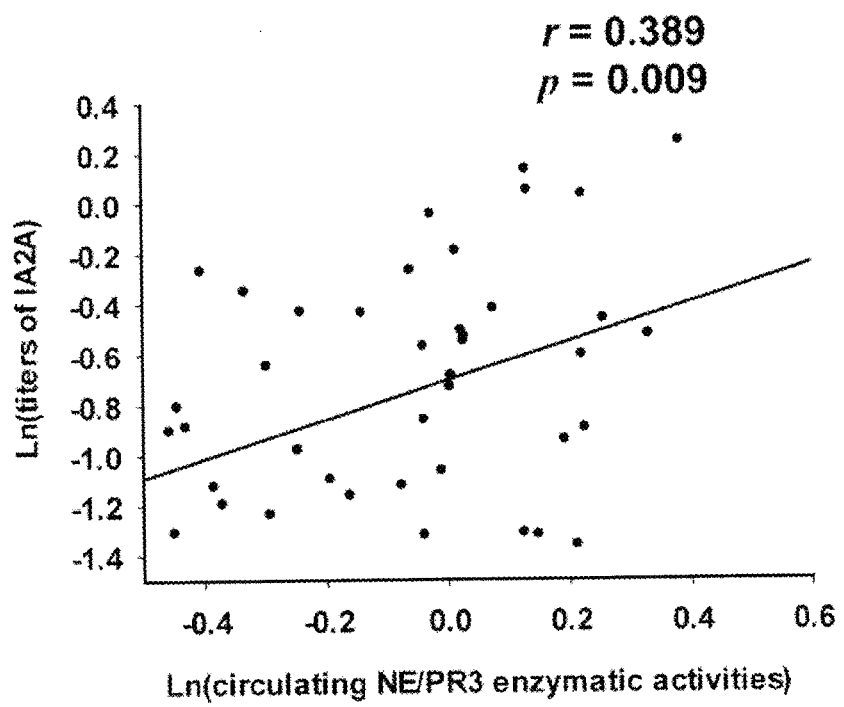

Furthermore, the relationship between circulating neutrophil serine proteases and the three autoantibodies associated with β-cell autoimmunity in T1D patients, including GADA, IA2A and ZnT8A, were investigated in the study cohort. Among 149 T1D patients, 54 (36%) were autoantibody-negative, 61 (41%), 24 (16%), and 10 (7%) had one, two and three autoantibodies-positive, respectively. Notably, circulating levels of both NE and PR3 proteins as well as their enzymatic activities were increased progressively with increased numbers of the autoantibodies detected in these patients (FIG. 4 (A-C)). Even for the autoantibody-negative T1D patients, the circulating protein levels and enzymatic activities of both NE and PR3 were much higher than those in healthy controls [protein levels: NE: 1154.90 (770.8-1749.5) vs 397.0 (262.2-468.8) ng/ml, p<0.0001; PR3: 237.4 (154.3-307.1) vs 107.4 (92.5-165.0) ng/ml, p<0.0001; enzymatic activities: 0.53 (0.37-0.79) vs 0.14 (0.10-0.21) mU/ml, p<0.001] (FIG. 4 (A-C)). Furthermore, a strong correlation between the titers of GADA and the circulating protein levels of NE (r=0.296, p=0.011) and PR3 (r=0.270, p=0.021) as well as NE/PR3 enzymatic activities (r=0.275, p=0.019) were detected in T1D patients with GADA-positive (n=73) (FIG. 4 (D-F)). Likewise, the titers of IA2A in T1D patients were also positively associated with the protein levels of NE, PR3 and their enzymatic activities (FIG. 5 (A-C)). On the contrary, no significant correlation between fasting blood glucose and circulating protein levels of NE (r=−0.103, p=0.211) or PR3 (r=−0.097, p=0.237) or NE/PR3 enzymatic activities (r=−0.078, p=0.342) was observed in the present study cohort. Taken together, these data suggested that elevated NE and PR3 may be causally associated with β-cell autoimmunity, but not glycemic status in T1D patients.

Example 4

Evaluation of Circulating Protein Levels of Murine Proteinase 3 in the Non-Obese Diabetic (NOD) Mice Animal Studies—
Non-obese diabetic (NOD) mice (The Jackson Laboratory), a well-established T1D animal model which is susceptible to spontaneous development of autoimmune insulin dependent diabetes mellitus (IDDM), are used for dynamic, consistent and chronic research on inter-relationship between neutrophil elastase, proteinase 3 and T1D development. The onset of T1D in NOD mice is characterized by a non-fasting plasma glucose level higher than 13.9 mmol/L. Since female NOD mice exhibit higher T1D incidences (60%-80%) than male (20-30%), the investigation mainly focus on female ones. Female NOD mice (n=7) were monitored weekly for body weight, blood glucose measurement and serum collection from 3-week old. The mice were kept under 12-hour light-dark cycles at 22 to 24° C., with ad libitum access to water and standard chow (PicoLab Rodent Diet 20, LabDiet). All animal experimental procedures were approved by the Committee on the Use of Live Animals for Teaching and Research of the University of Hong Kong and were carried out in accordance with the Guide for the Care and Use of Laboratory Animals.

Results—

Figure 6:
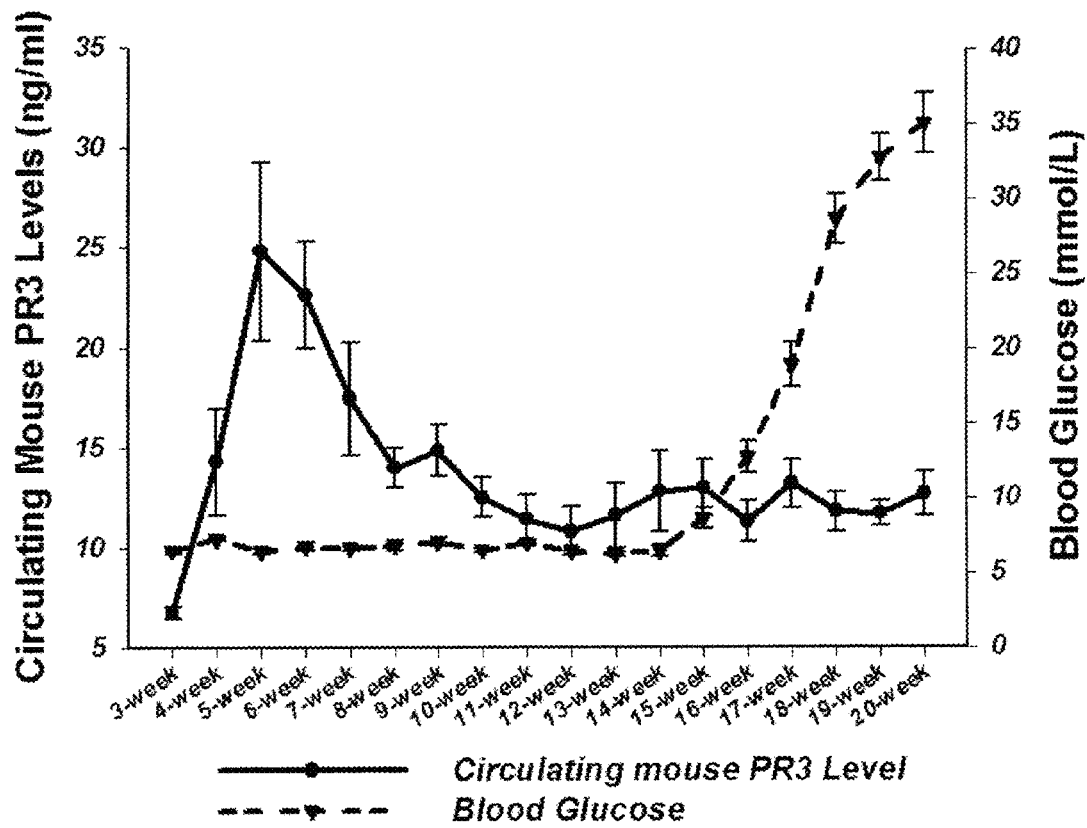
FIG. 6 is a graph showing the dynamic changes of circulating protein levels of mouse PR3 and blood glucose during diabetic development in NOD mice (n=7).

Circulating mouse proteinase 3 protein levels were measured using in-housed developed sandwich ELISA kits as described in Example 2. It is shown that overt hyperglycemia was not observed in NOD mice until 16-week old whereas proteinase 3 protein levels in circulation started to increase at a very early stage (3-week: 6.71 (5.70-7.19) ng/ml versus 4-week: 14.309 (7.28-25.75) ng/ml, $p<0.05$) and peak around 6-week (3-week: 6.71 (5.70, 7.19) ng/ml versus 6-week: 22.61 (15.15-31.174) ng/ml, $p<0.001$, (FIG. 6)), suggesting that circulating PR3 may serve as a sensitive predictive biomarkers for T1D development.

DISCUSSION

The current diagnosis of T1D heavily relies on the detection of the autoantibodies against several β-cell-specific antigens. However, in children these autoantibodies are rarely detectable before six months of age (Ziegler et al., 1999). Moreover, the diagnostic sensitivity of the single autoantibody measurement in T1D patients is as low as 59%-67% (Lebastchi and Herold, 2012). To capture the therapeutic window for this disease, it is critically important to identify new biomarkers for detection of early immunological events that affect the islets.

It has been discovered that a modest reduction of neutrophil counts in T1D patients is accompanied by a marked elevation of both protein levels and enzymatic activities of the two major neutrophil serine proteases NE and PR3. Furthermore, these changes in T1D patients are closely associated with increased neutrophil NETosis, as determined by quantification of MPO-DNA complexes in the circulation. These findings suggest that the reduction of neutrophil counts in T1D patients is attributed in part to augmented NETosis, which in turn leads to increased NET formation and release of NE and PR3 into the blood stream.

The amplitude of elevation in circulating NE/PR3 enzymatic activities and NET formation in patients with the disease duration of less than one year is substantially higher than those with disease duration of more than one year. A significant reduction in neutrophil counts is observed only in T1D patients with disease duration of less than one year. Consistent with our findings, a previous study in Italy also found that neutrophil reduction is greatest in individuals with the highest risk of developing T1D (Valle et al., 2013). After the disease onset, mild neutropenia persists for a few years and then resolves at 5 years after diagnosis (as determined by a longitudinal analysis). In NOD mice with spontaneous development of autoimmune diabetes, neutrophil infiltration and NET formation in the islets are detected as early as two weeks after birth, well before the onset of overt diabetes (Diana et al., *Nat Med* 19:65-73 (2013)). Furthermore, neutrophil depletion at the early stage prevents further development of diabetes in NOD mice (Diana et al., 2013). Taken together, these data support a causal role of neutrophil NETosis, NET formation and augmented release of neutrophil serine proteases in the onset of β-cell autoimmunity in T1D. Indeed, increased neutrophil NETosis and NET formation have been implicated in a number of autoimmune diseases, including small vessel vasculitis (SVV), systemic lupus erythematosus (SLE), and multiple sclerosis (Kessenbrock et al., 2009; Naegele et al., *Journal of neuroimmunology* 242:60-71 (2012); Villanueva et al., *Journal of immunology* 187:538-552 (2011)).

Furthermore, elevated NE and PR3 are significantly associated with the positive numbers and titers of the autoantibodies detected in T1D patients. Even in those autoantibody-negative patients, the circulating enzymatic activities of NE and PR3 are still substantially higher than healthy controls, suggesting that serum NE and PR3 may serve as sensitive biomarkers for early detection of those individuals with high risk of developing T1D. On the other hand, we found no significant association between increased serum levels of NE and PR3 and the severity of hyperglycemia in T1D patients. In fact, while hyperglycemia becomes more severe with the progression of T1D, serum levels of NE and PR3 exhibit opposite changes, suggesting that increased neutrophil NETosis and augmented release of NE and PR3 are not the consequence of impaired glycemic controls, but are related to β-cell autoimmunity. In line with this notion, reduced neutrophil counts have been observed in non-diabetic first degree relatives of patients with T1D (Valle et al., 2013).

In addition to its classical roles for host defense against infection, neutrophil serine proteases are important regulator of inflammation and innate immunity (Meyer-Hoffert, *Front Biosci (Landmark Ed)* 14:3409-3418 (2009); Meyer-Hoffert and Wiedow, 2011; Pham, *Nat Rev Immunol* 6:541-550 (2006); Wiedow and Meyer-Hoffert, 2005). Both NE and PR3 are involved in maturation and release of pro-inflammatory cytokines such as TNFα, IL-1β and IL-18, and also induces expression and activation of Toll-like receptors (Coeshott et al., *Proceedings of the National Academy of Sciences of the United States of America* 96:6261-6266 (1999); Devaney et al., *FEBS Lett* 544:129-132 (2003); Devaney et al., *FEBS Lett* 544:129-132 (2003); Walsh et al., *J Biol Chem* 276:35494-35499 (2001)), all of which are important mediator of insulitis and β cell destruction (Grieco et al., *Semin Immunopathol* 33:57-66 (2011); Padgett et al., *Annals of the New York Academy of Sciences* 1281:16-35 (2013)). Furthermore, NE and PR3 play an indispensable role in recruiting neutrophils to the site of inflammation. Notably, neutrophil serine proteases have recently been implicated in high fat diet-induced obesity, inflammation and macrophage infiltration in adipose tissues in mice (Talukdar et al., *Nat Med* 18:1407-1412 (2012)). Injection of recombinant PR3 alone is sufficient to induce hyperglycemia in mice (Bae et al., *Endocr Res* 37:35-45 (2012)). By contrast, treatment with A1AT, a major endogenous inhibitor of NE and PR3, decreases lymphocyte infiltration in the islets, and prevents 0 cell loss and diabetes in rodent models of T1D (Lu et al., *Human gene therapy* 17:625-634 (2006); Song et al., *Gene therapy* 11:181-186 (2004)). These animal studies, in conjunction with the present clinical findings, suggest that elevated NE and PR3 may be the direct contributors to the pathogenesis of autoimmune diabetes by initiating and/or perpetuating autoimmune inflammatory responses in pancreatic islets.

A1AT, the most abundant circulating serpin secreted from hepatocytes, inhibits neutrophil serine proteases by covalent binding to the enzymes (Janciauskiene et al., *Respiratory medicine* 105:1129-1139 (2011)). Deficiency of A1AT has been implicated in a number of inflammatory disorders such as chronic obstructive pulmonary disease (Stoller and Aboussouan, *Lancet* 365:2225-2236 (2005)). The present study observed a modest, but significant reduction of circulating A1AT in patients with T1D, suggesting that augmented circulating NE and PR3 activities may result from a combination of increased release of these two enzymes from neutrophils NETosis and decreased production of their endogenous inhibitor A1AT.

Taken together, the data provided herein has provided the first evidence supporting that augmented circulating NE and PR3 activities may result from a combination of increased release of these two enzymes from neutrophils NETosis and decreased production of their endogenous inhibitor A1AT in T1D, and elevated NE and PR3 may be the direct contributors to the pathogenesis of autoimmune diabetes by initiating and/or perpetuating autoimmune inflammatory responses in pancreatic islets. These results collectively demonstrate that NE and PR3 are the potential biomarkers for prediction and early diagnosis of T1D as well as for differential diagnosis of T1D from other types of diabetes.

It is understood that the disclosed methods and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a substrate" includes a plurality of such substrates; reference to "the substrate" is a reference to one or more substrates and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed methods and compositions belong. Although any methods and materials similar or equivalent to those described herein can be used in the practice or testing of the present methods and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different diabetes prevention treatments does not indicate that the listed diabetes prevention treatments are obvious one to the other, nor is it an admission of equivalence or obviousness.

Those skilled in the art will recognize, or be able to ascertain using no more than routine experimentation, many equivalents to the specific embodiments of the methods and compositions described herein. Such equivalents are intended to be encompassed by the following claims.

We claim:

1. A method for determining, in a sample obtained from a subject, whether:
   (a) the level of neutrophil elastase and proteinase 3 proteins is above or below 988.4 ng/ml or 206.0 ng/ml, respectively; and
   (b) the combined enzymatic activity of neutrophil elastase and proteinase 3 is above or below 0.41 mU/ml;
   the method comprising the steps of:
   obtaining the sample from the subject;
   measuring the enzymatic activities and/or protein levels of neutrophil elastase and proteinase 3 proteins in the sample; the step of measuring comprising:
   (a) contacting the sample from the subject with antibodies against neutrophil elastase and proteinase 3 for a time and under conditions allowing the formation of antigen-antibody complexes between neutrophil elastase and proteinase 3 proteins present in the sample with the corresponding antibodies, and quantifying the antigen-antibody complexes to determine the levels of neutrophil elastase and proteinase 3 proteins; and
   (b) contacting the sample from the subject with an appropriate substrate under appropriate conditions and determining the combined activity of neutrophil elastase and proteinase 3 based on the conversion of the substrate into a product; and determining whether the level of neutrophil elastase and proteinase 3 proteins is above or below 988.4 ng/ml or 206.0 ng/ml, respectively, and whether the combined enzymatic activity of neutrophil elastase and proteinase 3 is above or below 0.41 mU/ml.

2. The method of claim 1, wherein the protein levels of neutrophil elastase and proteinase 3 in the sample are measured by immunoassays.

3. The method of claim 1, wherein the sample is selected from blood, serum, plasma, urine, saliva, cerebrospinal fluid, tears, tissues, and combinations thereof.

4. The method of claim 1, wherein one or more islet-specific autoantibodies against glutamic acid decarboxylase (GADA), insulinoma-associated protein 2 autoantibody (IA-2A), and zinc transporter 8 antibody (ZnT8A) are not detectable in the subject.

5. The method of claim 1, wherein one or more islet-specific autoantibodies GADA, IA2A or ZnT8A are detectable in the subject.

6. The method of claim 1, wherein the subject has one or more risk factors for autoimmune diabetes.

7. The method of claim 1, wherein the subject is a child or adolescent.

8. The method of claim 1, wherein the subject is an adult.

9. The method of claim 1, wherein the subject is diagnosed with diabetes.

10. The method of claim 1, wherein the sample is selected from blood, serum, plasma, urine, saliva, cerebrospinal fluid, tears, tissues, and combinations thereof.

11. The method of claim 1, wherein the levels of neutrophil elastase and proteinase 3 proteins and the combined activity of neutrophil elastase and proteinase 3 proteins is determined in the blood, serum, or plasma sample of the subject.

12. A method for determining, in a sample obtained from a subject, whether:
  (a) the level of neutrophil elastase and proteinase 3 proteins is above or below 770.8 ng/ml or 154.0 ng/ml, respectively; and
  (b) the combined enzymatic activity of neutrophil elastase and proteinase 3 is above or below 0.37 mU/ml;
  the method comprising the steps of:
  obtaining the sample from the subject; and
  measuring the enzymatic activities and protein levels of neutrophil elastase and/or proteinase 3 proteins in the sample; the step of measuring comprising:
  (a) contacting the sample from the subject with antibodies against neutrophil elastase and proteinase 3 for a time and under conditions allowing the formation of antigen-antibody complexes between neutrophil elastase and proteinase 3 proteins present in the sample with the corresponding antibodies and quantifying the antigen-antibody complexes to determine the levels of neutrophil elastase and proteinase 3 proteins; and
  (b) contacting the sample from the subject with an appropriate substrate under appropriate conditions and determining the combined activity of neutrophil elastase and proteinase 3 based on the conversion of the substrate into a product; and
  determining whether the level of neutrophil elastase and/or proteinase 3 proteins is above or below 770.8 ng/ml or 154.0 ng/ml, respectively, and whether the combined enzymatic activity of neutrophil elastase and proteinase 3 is above or below 0.37 mU/ml,
  wherein antibodies against GADA, IA2A or ZnT8A are not detectable in the subject.

13. The method of claim 12, wherein the levels of neutrophil elastase and proteinase 3 proteins and the combined activity of neutrophil elastase and proteinase 3 proteins is determined in the blood, serum, or plasma sample of the subject.

14. The method of claim 12, wherein the subject has one or more risk factors for autoimmune diabetes.

15. The method of claim 12, wherein the subject is a child or adolescent.

16. The method of claim 12, wherein the subject is an adult.

17. The method of claim 12, wherein the subject has diabetes.

18. The method of claim 12, wherein the sample is selected from blood, serum, plasma, urine, saliva, cerebrospinal fluid, tears, tissues, and combinations thereof.

19. A method for determining whether a subject is at risk of developing autoimmune diabetes comprising:
  (a) obtaining a sample from said subject;
  (b) determining whether a combined enzymatic activity of neutrophil elastase and proteinase 3 is above or below 0.37 mU/ml by contacting the sample from the subject with an appropriate substrate under appropriate conditions and determining the combined enzymatic activity of neutrophil elastase and proteinase 3 based on the conversion of the substrate into a product;
  (c) obtaining a second sample from said subject;
  (d) determining immunoreactivity against GADA, IA2A or ZnT8A antibodies from said second sample,
  wherein the subject is at risk of developing autoimmune diabetes if the combined enzymatic activity exceeds 0.37 mU/ml and no GADA, IA2A and ZnT8A is detected.

20. A method for determining whether a subject is at risk of developing autoimmune diabetes comprising:
  (a) obtaining a sample from said subject;
  (b) determining whether a combined enzymatic activity of neutrophil elastase and proteinase 3 is above or below 0.37 mU/ml by contacting the sample from the subject with an appropriate substrate under appropriate conditions and determining the combined enzymatic activity of neutrophil elastase and proteinase 3 based on the conversion of the substrate into a product;
  wherein the subject is at risk of developing autoimmune diabetes if the combined enzymatic activity exceeds 0.37 mU/ml.

* * * * *

UNITED STATES PATENT AND TRADEMARK OFFICE
CERTIFICATE OF CORRECTION

PATENT NO. : 9,625,460 B2
APPLICATION NO. : 14/725101
DATED : April 18, 2017
INVENTOR(S) : Aimin Xu et al.

Page 1 of 1

It is certified that error appears in the above-identified patent and that said Letters Patent is hereby corrected as shown below:

In the Specification

Column 32,
Line 62, "prevents 0 cell" should read --prevents β cell--.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*